United States Patent [19]
Priester et al.

[11] Patent Number: 5,568,209
[45] Date of Patent: Oct. 22, 1996

[54] AUTOMATED POCKET-SIZED NEAR VISION TESTER

[76] Inventors: William B. Priester, 3449 Lake Pointe, Memphis, Tenn. 38125; Maxwell Cutler, 4991 Chickasaw, Memphis, Tenn. 38117

[21] Appl. No.: 424,153

[22] Filed: Apr. 17, 1995

[51] Int. Cl.$^6$ ......................................... A61B 3/02
[52] U.S. Cl. ........................ 351/243; 351/244; 351/246; 351/239
[58] Field of Search .................... 351/239, 243, 351/244, 246

[56] References Cited

U.S. PATENT DOCUMENTS

| | | | |
|---|---|---|---|
| H000293 | 6/1987 | Task | 351/243 |
| 686,535 | 11/1901 | Reese . | |
| 1,630,281 | 5/1927 | Tillyer . | |
| 1,874,986 | 4/1930 | Harker . | |
| 2,282,494 | 5/1942 | Potter . | |
| 2,573,546 | 10/1951 | Costenbader . | |
| 4,550,990 | 11/1985 | Trispel | 351/243 |
| 4,572,630 | 2/1986 | Task | 351/243 |
| 4,740,072 | 4/1988 | Griffin | 351/243 |
| 5,078,486 | 1/1992 | Evans | 351/243 |
| 5,121,981 | 6/1992 | Waltuck | 351/243 |
| 5,129,720 | 7/1992 | Jovicevic | 351/243 |
| 5,220,362 | 6/1993 | Blenkle | 351/235 |
| 5,325,136 | 6/1994 | Salibelle | 351/243 |
| 5,398,085 | 3/1995 | Hofeldt | 351/243 |
| 5,416,540 | 5/1995 | Hayashi | 351/243 |

OTHER PUBLICATIONS

Gassovskii et al., "An instrument for testing vision and prescribing eyeglasses for close work", Mar. 1976, pp. 163–165.

Sheldrick, et al., "Study of Diagnostic Accord Between General Practitioners and An Ophthalmologist," British Medical Journal, vol. 304, pp. 1096–1098 (1992).

Shah, et al., "Measurement of Visual Acuity by Hospital Physicians," Postgraduate Medical Journal (England), vol. 69, p. 595 (1993).

VectorVision CSV–1000 Product Brochure (patented by Evans, U.S. Pat. No. 5,078,486), Jan. 7, 1992.

*Primary Examiner*—William L. Sikes
*Assistant Examiner*—James A. Dudek

[57] ABSTRACT

A lightweight, pocket-sized, hand-held near vision test apparatus that selectively retroilluminates different near vision test objects located on an interchangeable near vision test card, or alternatively, selectively displays near vision test objects on a flat panel display screen. The apparatus allows the examiner to electronically direct the patient's attention to selected near vision test objects, while providing a baseline amount of contrast illumination.

27 Claims, 21 Drawing Sheets

FIGURE 3
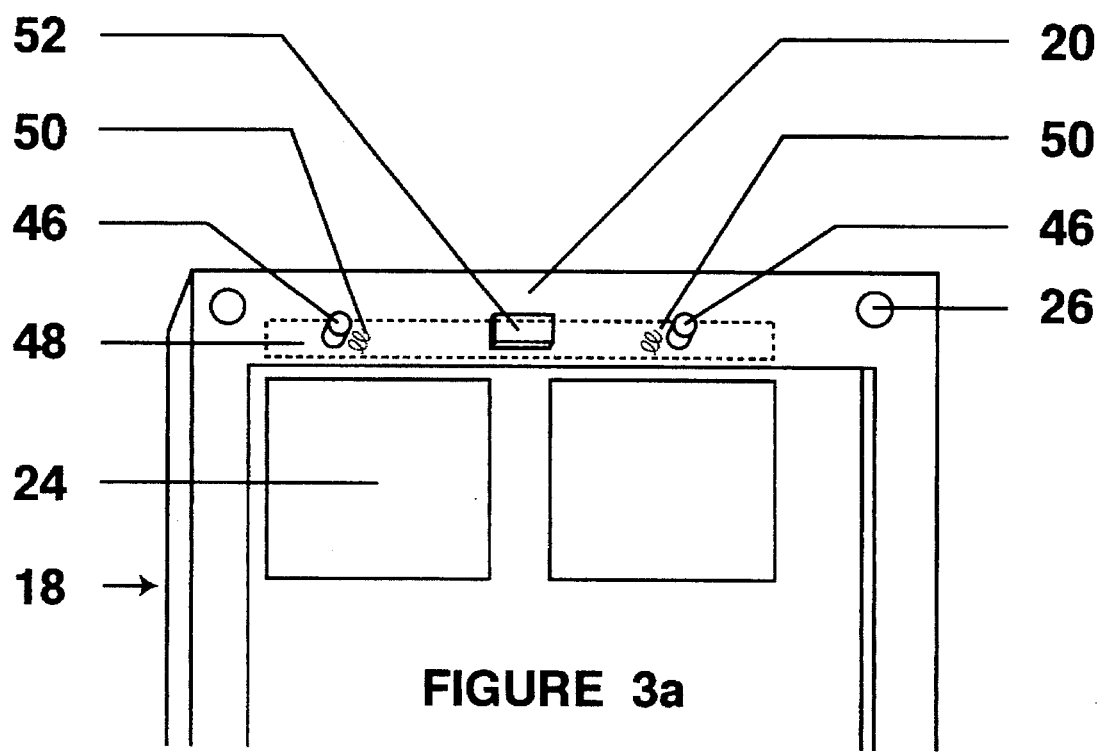
FIGURE 3a
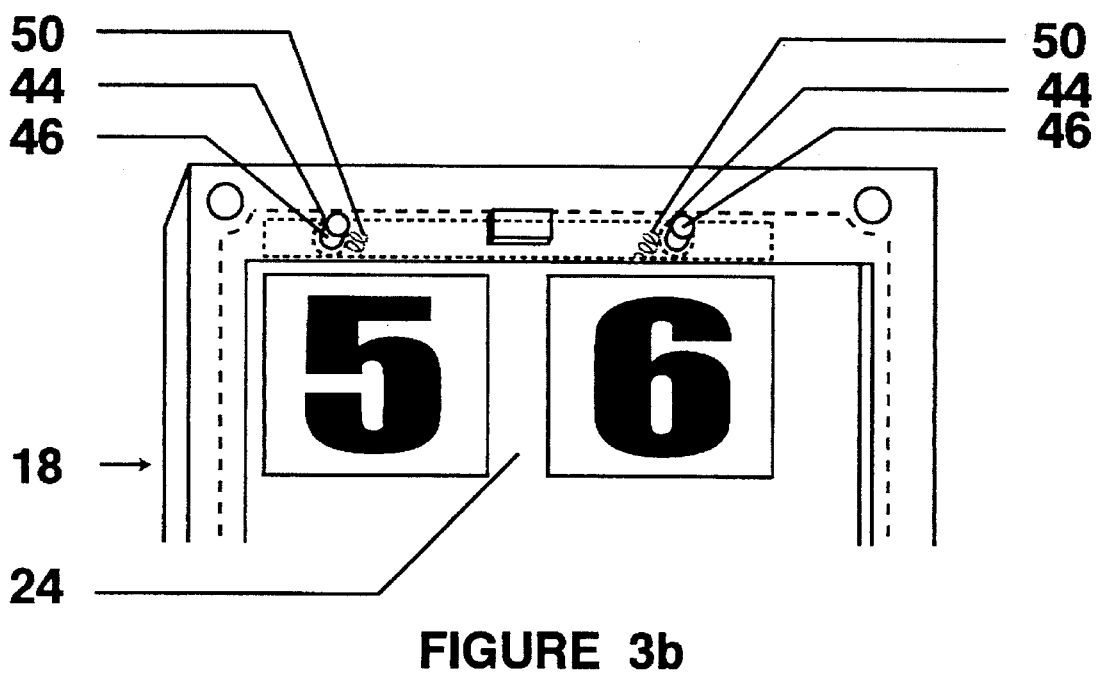
FIGURE 3b

6 8 3

H T V

E m Ǝ

⊂ ⊃ C

◻ ◻ X

FIGURE 16
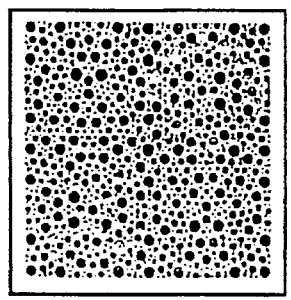
HR Color Test Panel
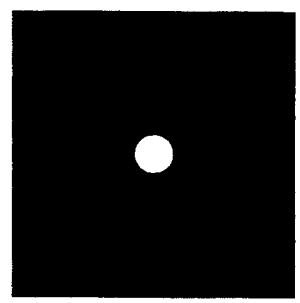
White Fixation Spot
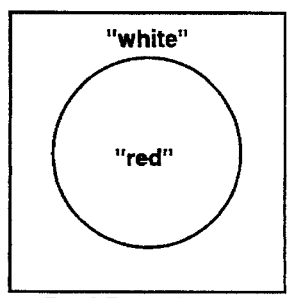
Red Test Panel
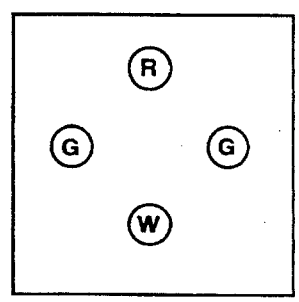
Worth Four Dots
R=Red, G=green,
W=white
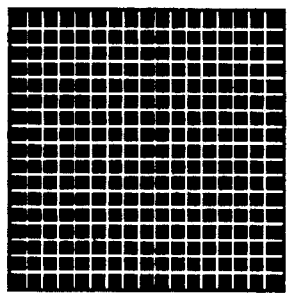
Amsler Grid
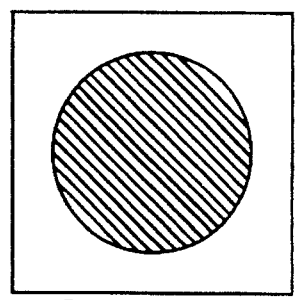
Contrast Test Panel
Motion Picture Panel
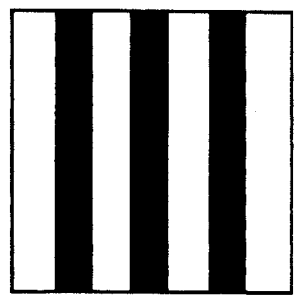
Optokinetic Motion Panel

FIGURE 17

| | |
|---|---|
| VA | visual acuity |
| PH | penhole |
| cc | with correction |
| sc | without correction |
| NC | near card |
| P | pupils |
| EOMI | extraocular movements intact |
| ortho | eyes alligned properly |
| VFF | visual fields full |
| SLE | slit lamp exam |
| L/L | lids and lashes |
| C/S | conjunctiva and sclera |
| K | cornea |
| AC | anterior chamber |
| AV | anterior vitreous |
| C&F | cell and flare |
| D&Q | deep and quiet |
| KP | keratic precipitates |
| BK | bullous keratopathy |
| SPK | superficial punctate keratopathy |
| SEI | sub-epithelial infiltrate |
| C/D | cup to disk ratio |
| PVD | posterior vitreous detachment |
| ST | superior-temporal |
| IT | inferior-temporal |
| SN | superior-nasal |
| IN | inferior-nasal |
| CWS | cotton wool spot |
| D/B Heme | dot and blot hemorrhages |
| HE | hard exudates |
| MA | microaneurysm |
| IRMA | intra-retinal microvascular abnormalities |
| ME | macular edema |
| CME | cysytoid macular edema |
| CSME | clinically significant macular edema |
| NVD | neovascularization of the disk |
| NVE | neovascularization elsewhare |
| NVI | neovascularization of the iris |
| RD | retinal detachment |
| TRD | traction retinal detachment |
| COAG | chronic open angle glaucoma |
| NAG | narrow angle glaucoma |
| NVG | neovasular glaucoma |
| BGDR | background diabetic retinopathy |
| PPDR | pre-proliferative diabetic retinopathy |
| PDR | proliferative diabetic retinopathy |

FIGURE 19
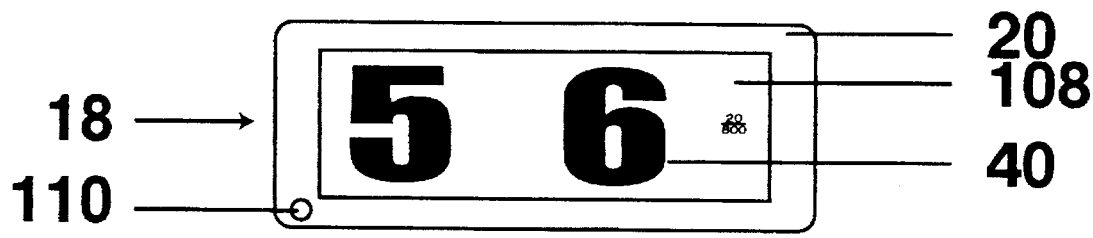
FIGURE 19a
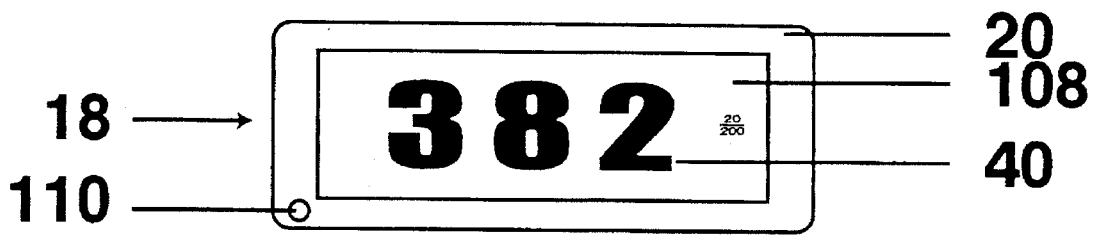
FIGURE 19b
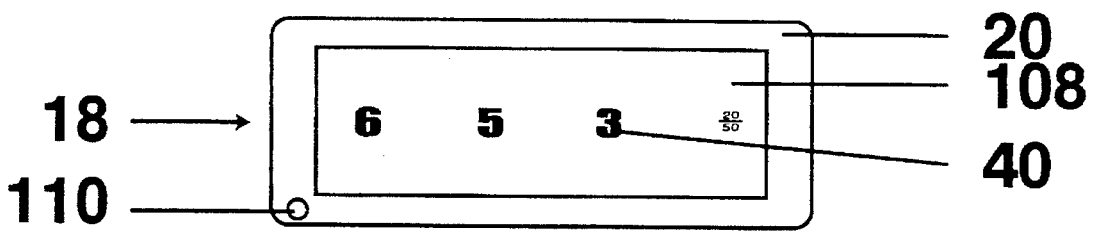
FIGURE 19c

130 — — 32

134 — — 32
136 —

AUTOMATED POCKET-SIZED NEAR VISION TESTER

FIELD OF THE INVENTION

This invention relates to the field of vision testing instruments, specifically to an advancement in the testing of near vision by healthcare examiners by providing a portable electronic pocket-sized near vision tester that features automated selective retroillumination of designated near vision test objects, thereby allowing the examiner to actively direct the patient's attention to selected near vision test objects.

BACKGROUND OF THE INVENTION

Visual acuity is a primary concern for both the patient and the healthcare professional. Proper measurement of visual acuity is of paramount importance in detecting disease of the visual system and should be included in every general physical exam. Unfortunately, visual acuity remains one of the least monitored parameters of health in the healthcare community. J. H. Sheldrick et al. published a study entitled "Study of diagnostic accord between general practitioners and an ophthalmologist" in volume 304, pp. 1096–8 of the 1992 British Medical Journal. Of 1103 patients who visited a general physician with an eye complaint, visual acuity was recorded in the medical record for only 114 of the patients. This low visual acuity testing rate of approximately 10% occurred in spite of the fact that the study questionnaire specifically asked the general physician if visual acuity was assessed.

P. Shah et al. published a study entitled "Measurement of visual acuity by hospital physicians" in volume 69(813), p. 595 of the 1993 Postgraduate Medical Journal (England). In that study, 102 hospital physicians were asked four basic questions about testing visual acuity, and only 24.5% of the doctors answered all four questions correctly. Ninety-three percent could name the distance visual acuity chart, known as the Snellen chart. Seventy percent knew that the correct distance of twenty feet should be used between the chart and the patient. Fifty-six percent knew how to obtain a rough estimate of visual acuity if the patient did not have their spectacle correction available. Only 63% were able to correctly record the visual acuity of a highlighted line on a Snellen chart pictured in the questionnaire.

The Sheldrick study and the Shah study raise questions of why visual acuity is tested so infrequently by the general physician and why so little is known about how to do it properly. First and foremost, the proper measurement of visual acuity is a time-consuming process. If healthcare professionals were given a faster, more convenient, more reliable, and more portable way to test visual acuity, the visual acuity testing rate would increase dramatically. Second, healthcare providers must be educated concerning the importance of screening their patients for decreased visual acuity. As healthcare reform proceeds, primary healthcare providers will assume more and more responsibility for determining when their patients need to be referred to an eyecare specialist, and therefore will have a greater responsibility to test the visual acuity of their patients.

While the Snellen chart has long been the standard for testing vision in the office, the Rosenbaum Pocket Vision Screener has been the standard for testing vision in emergency rooms and hospitals. The Rosenbaum Pocket Vision Screener and other similar pocket-sized near vision testers consist of thin cards, approximately 6.25 inches by 3.5 inches by 0.04 inch, made of plastic, cardboard, or laminated cardboard. Near vision test objects consisting of numbers, letters, pictures, or symbols of different sizes are arranged in rows on the front face of these pocket-sized near vision test cards. The largest sized test objects are located in the top row of the card with progressively smaller test objects arranged in rows proceeding down the card.

The near vision test is performed by holding the near vision test card 13 to 16 inches from the patient's eyes, depending on which style of near vision test card is being used. The patient's left eye is covered and the patient is asked to read the smallest line possible with his or her right eye. Then, the patient's right eye is covered and the patient is asked to read the smallest row possible with his or her left eye. While holding the card, the examiner is positioned to the side of the patient in order that: a) the patient may be monitored for proper fixation and occlusion, and b) the front face of the test card may be monitored for the correctness of test responses.

Given their thinness and rectangular shape, pocket near vision testers are easily carried in the pocket of a healthcare professional's coat. This pocket-sized portability affords the healthcare professional a much easier means of testing vision in acute or chronically ill patients than could ever be achieved by using the bulkier Snellen chaff at a distance of 20 feet. Other pocket vision testers, such as Reese, U.S. Pat. No. 686,535 and Costenbader, U.S. Pat. No. 2,573,546, use test disks that are dialed manually by the examiner to bring various near vision test objects into view. However, these testers are awkward to use and did not achieve much commercial success.

Near vision test cards also may be used in the eyecare professional's office where they can be removably mounted on the protruding reading card rod of a phoropter. A phoropter is an ophthalmic refracting apparatus which is typically mounted on an adjustable arm next to the patient examining chair. The protruding reading card rod of the phoropter is ruled in inches and centimeters and has a sliding attachment means for removably securing near vision test cards. The phoropter has many different optical lenses that allow the examiner to assess a patient's refractive error. The patient's distance refractive error is the sum total and orientation of lens power needed to focus the patient's vision at twenty feet or more. The patient's near refractive error is the sum total and orientation of lens power needed to focus the patient's vision at fourteen inches. Once appropriate lenses are in place to focus the patient's vision at or near fourteen inches, a near vision test card is attached to the protruding reading card rod of the phoropter, and the card is positioned to refine this focus and to measure the best corrected near visual acuity.

A significant problem in using a near vision test card on a phoropter is the lack of satisfactory illumination of the test card. Currently, the majority of eyecare professionals use external lighting sources located on hinged positioning arms. These lamps must be positioned by the examiner for each patient, and therefore require time and effort to set up. The end result is an amount of light striking the near vision test card which is by no means standardized or reproducible. Potter, U.S. Pat. No. 2,282,494, and Blenkle, U.S. Pat. No. 5,220,362, attempted to address this problem. However, given their bulky design, these external illumination systems are not suited for portable use in hospitals and emergency rooms.

In the field of visual acuity testing, there are many large office or desktop-sized near and distance vision testing devices, such as described in patents by Griffin et al., U.S.

Pat. No. 4,740,072, Waltuck et al., U.S. Pat. No. 5,121,981, and Jovicevic, U.S. Pat. No. 5,129,720 as well as in the Soviet Journal of Optical Technology (March 1976) by Gassovskii et al. These devices are used to test the visual acuity of persons who can be positioned at a testing station. They are not easily transported by healthcare professionals from one hospital room or emergency room to the next. There are also many different kinds of projector-type vision testing devices that are used to test distance visual acuity in the office setting. These devices are even less easily portable than the desk-top models. The size of these desk-top and projector-type vision testing devices severely limits their use in hospitals and emergency rooms in that acute or chronically ill patients would have to be seated at a test station to have their vision tested.

It is much easier to use a hand-held, lightweight, pocket vision test card with acute or chronically ill patients. These test cards, as described above, are positioned in front of the patient's eye without changing the patient's position. However, in many clinical situations, there are numerous practical difficulties in using these cards at the bedside or chairside. First, the pocket near vision test cards in present use are not illuminated. If inadequate illumination is available, the patient must be moved to an area of better illumination, or a source of illumination must be directed on the card (usually a penlight from the examiner's pocket). The use of a penlight occupies one of the examiner's hands that he might need to perform other tasks associated with near vision testing. Second, the patient's attention span often is decreased because of illness or injury, and the examiner must somehow direct and maintain the patient's attention on the section of the card being used. This is usually accomplished by the examiner placing his or her thumb below the row in question thereby occluding the row below and forming an incomplete frame of the row in question. The penlight is then focused on the row or test object in question and the patient is asked to read the row or identify the test object. Many eyecare professionals use brightly colored felt-tip pens to draw frames around the individual rows or test objects that they use to test cognitively or speech-impaired patients. Alternatively, a second health worker may point at the desired row or test object while the examiner holds the card and directs the penlight. Third, if the patient is unable to cover his or her own eye, a patch must be applied or another hand must be used to cover the eye. Fourth, if the patient is unable to open the eye to be tested, the eye must be opened with the examiner's fingers or with some sort of mechanical eyelid retractor. In the case of the severely swollen eye (such as seen in severe trauma, infection, tumors, or inflammatory disorders), the eyelids must be gently pried apart with two hams operating two separate eyelid retractors. Finally, the card must be held by someone (preferably the examiner) at the correct distance and in the proper orientation.

In the worst case scenario (a patient with decreased mental status, one severely swollen eye, and unable to use his or her own hams), the examiner might need a total of six hands: (1) one to hold the card, (2) one to hold the penlight, (3) one to direct the attention of the patient to the proper section or individual test object on the card, (4) one to cover the untested eye, and (5–6) two to open the swollen eye. This invention allows the healthcare professional to perform the first four tasks listed above without an assistant.

SUMMARY OF THE INVENTION

The present invention is a lightweight, pocket-sized, hand-held near vision test apparatus. This apparatus greatly simplifies the testing of near vision in acute or chronically ill patients by allowing the examiner to direct the patient's attention around a near vision test card attached to the apparatus by selectively retroilluminating (i.e., illuminating from behind) particular test objects on the test card. The examiner does this by operating a small panel of pushbuttons on the back of the apparatus with the index finger of the hand that is holding the apparatus. The ability to operate the apparatus with one hand frees the examiner's other hand for performing the other tasks associated with vision testing, which were described previously.

The translucent near vision test cards may be rapidly interchanged with other test cards through a mechanical locking and release means, thereby allowing the examiner to match the near vision test with the patient's cognitive level. For instance, if the patient is a small child, a test card with Allen figures (pictures of small, simple everyday objects) may be inserted and secured in the test apparatus. If the patient is illiterate, a card with Landolt rings or tumbling E's may be inserted, and so on.

The near vision test objects on the test card may be selectively retroilluminated by electroluminescent panels, light emitting diodes, incandescent or fluorescent lamps, or by other well-known means of generating light. Alternatively, the vision test objects (as well as advanced vision test panels and reference tables) may be displayed and illuminated by flat panel displays such as plasma, liquid crystal, electroluminescent, ferro-electric, thin film transistor ("TFT"), or other similar displays. In the flat panel display embodiments, near vision test objects are generated electronically, and the displayed test objects may be changed electronically without the need to change test cards.

It also is possible to use a transmissive liquid crystal panel, ferro-ceramic panel, or similar planar device as a "light gate" or selective light shutter positioned between the light source and the test objects, and to control the light gate to selectively transmit light so as to retroilluminate only particular selected test objects. One or several light sources provide light that is typically blocked by the light gate when it is in a non-transmission mode and therefore is opaque to light. Test objects are selectively retroilluminated by controlling the light gate, using a microcontroller, to enable the transmission of light through selected areas on the light gate that correspond to the particular test objects positioned adjacent to those areas. This mechanism avoids the need for separate light sources for each test object or set of test objects, and it minimizes or eliminates the switching circuitry associated with each light source.

Self-illuminated flat panel displays such as thin film transistor, electroluminescent, or plasma displays also may be used to retroilluminate near vision test objects on a test card. For example, a test card may be positioned above or in front of a self-illuminated flat panel display. The flat panel display is controlled to selectively illuminate the particular areas on the flat panel display that correspond to the test objects positioned in front of those areas, thereby selectively retroilluminating the test objects. This mechanism avoids the need for separate light sources for each test object or set of test objects, and it minimizes or eliminates the switching circuitry associated with each light source. Optionally, the flat panel display may be used without the test card to display vision test objects, abbreviations, or other information.

The test cards and the flat panel displays may be color or black and white, depending on the intended use. Visual acuity test objects range in size from 20/800 to 20/20, as expressed in distance visual acuity equivalents. A visual acuity of 20/60 means the patient can see at 20 feet what a person with normal vision can see at 60 feet. In other words, the smaller the denominator, the better the vision. Although there are other ways of discussing and recording visual acuity, this notation system is the standard in the medical community as well as among the lay public.

The examiner operates pushbutton switches on the apparatus to control the selective retroillumination of vision test objects on the interchangeable, translucent near vision test card, or to selectively display test objects on a flat panel display. The examiner may operate the switches to provide a number of retroilluminating or display options such as: (1) "change row," (2)"change column," (3)"intensive care," (4)"direction," (5)"all" test objects, (6) "randomize test objects," (7) "change style of test objects," (8) "change advanced vision test," and (9) "reference table." The preferred pushbutton switch is a momentary, non-locking switch, although latching switches, slide switches, membrane switches, touchscreens, or any switch known in the art may be used. Although the pushbutton switches are illustrated on the rear of the invention, they may be located on the sides or other surfaces of the invention for operation by the examiner.

The "intensive care" pushbutton allows the examiner to scroll from row to row and illuminate only one test object per row, which for this test is always a numeral 2, 3, 4, or 5. The low numerals allow patients who are mechanically-ventilated or otherwise speech-impaired to signal a nonverbal test response by using the fingers of one hand, blinking one or both eyes, or making other nonverbal gestures a certain number of times, thereby indicating cognition of the illuminated numeral.

In another application, the automated near vision tester may be attached to the commonly used wall or stand mounted units that house other eye and ear examination devices such as an ophthalmoscope and an otoscope. In the most common of these eye and ear examination units, the head of the ophthalmoscope rests in a forked power lever on one side of a centrally located rectangular power box. The otoscope is situated in a similar manner on the other side of the box. When either instrument is lifted from its power lever, the power lever moves up into a power-on position and electrical power is delivered to the instrument through a coiled, stretchable power cord. The front face of the rectangular power box is generally unoccupied. In this setting, the automated near vision test apparatus could be removably attached to the front face of the rectangular power box by means of a forked power lever, a cage designed to hold the tester, or by similar means. The forked power lever would serve as an on-off switch in the same manner as the power levers for the ophthalmoscope and otoscope. Upon lifting the automated near vision tester from its power lever attachment, power would be delivered to the vision tester through a coiled, stretchable power cord. Having the automated near vision tester readily available at the bedside in an emergency room or intensive care setting would greatly facilitate the proper testing of visual acuity.

In yet another application, the automated near vision tester may be removably mounted on the protruding reading card rod of a phoropter, also known as an ophthalmic refractor. Once appropriate lenses in the phoropter are adjusted to focus the patient's vision at or near fourteen inches, the automated near vision tester may be positioned to refine this focus and to measure best-corrected near visual acuity. The invention simplifies this near vision refractive test by providing a standard level of illumination without requiring time-consuming movements to position an external lighting source to illuminate the test card. The rapid selective retroillumination of near vision test objects using the invention saves valuable time for the examiner. Furthermore, the invention may be removed easily from its mounting attachment and carried in one's pocket to the emergency room or hospital ward for consultations or patient follow-up.

These advances will greatly increase the ease of properly testing near vision by eliminating several of the hands that are needed to do it correctly. In busy hospitals and emergency rooms, the fewer hands that are needed to execute a task, the more likely it will be accomplished. In busy offices and clinics, faster, more efficient exams are essential to maintain optimal patient flow, which in turn allows more time for patient education. The ultimate goal is to increase the frequency at which vision is properly tested in all patients. Hopefully, this will help prevent loss of vision secondary to visual system disease, which otherwise could have been treated successfully if it had been discovered earlier.

OBJECTS OF THE INVENTION

It is an object of the invention to provide a battery-powered near vision test unit which is easily transported in the pocket of the examiner's lab coat and which is held and operated by the same hand.

It is a further object to simplify the often difficult task of testing near vision by providing selective display or retroillumination (i.e., illumination from behind) of the test card in order to actively direct the patient's attention to particular test objects.

It is a further object to allow the examiner to control which test objects are retroilluminated or displayed by operating a small panel of pushbuttons on the back of the test unit.

It is a further object to provide an "intensive care" pushbutton which allows testing of mechanically-ventilated or otherwise speech-impaired patients.

It is a further object to allow for rapid exchanging of different translucent near vision test cards or to have an electronic means, such as a flat panel display, that allows rapid changing and randomization of vision test objects.

It is a further object to provide an extension cord powered version of the device for inclusion in wall or stand mounted eye and ear exam units or other integrated physical examination equipment.

It is yet a further object to provide an easy method of attaching the device to the protruding reading card rod of a phoropter.

These and further objects and advantages of our invention will become apparent from a consideration of the drawings and ensuing description.

BRIEF DESCRIPTION OF THE DRAWINGS

FIG. 3 illustrates an alternative test card locking mechanism both without (FIG. 3a) and with (FIG. 3b) a test card inserted.

FIG. 16 illustrates different advanced vision testing options available on a flat panel display embodiment of the invention.

FIG. 17 illustrates a table of ophthalmologic abbreviations available for display on a flat panel display embodiment of the invention.

FIG. 19 shows three front elevation views of a compact embodiment of the invention with a flat panel display that displays only one row of test objects at a time.

FIG. 19a illustrates the apparatus with the 20/800 row selected; FIG. 19b illustrates the apparatus with the 20/200 row selected; and FIG. 19c illustrates the apparatus with the 20/50 row selected.

Figure 1:
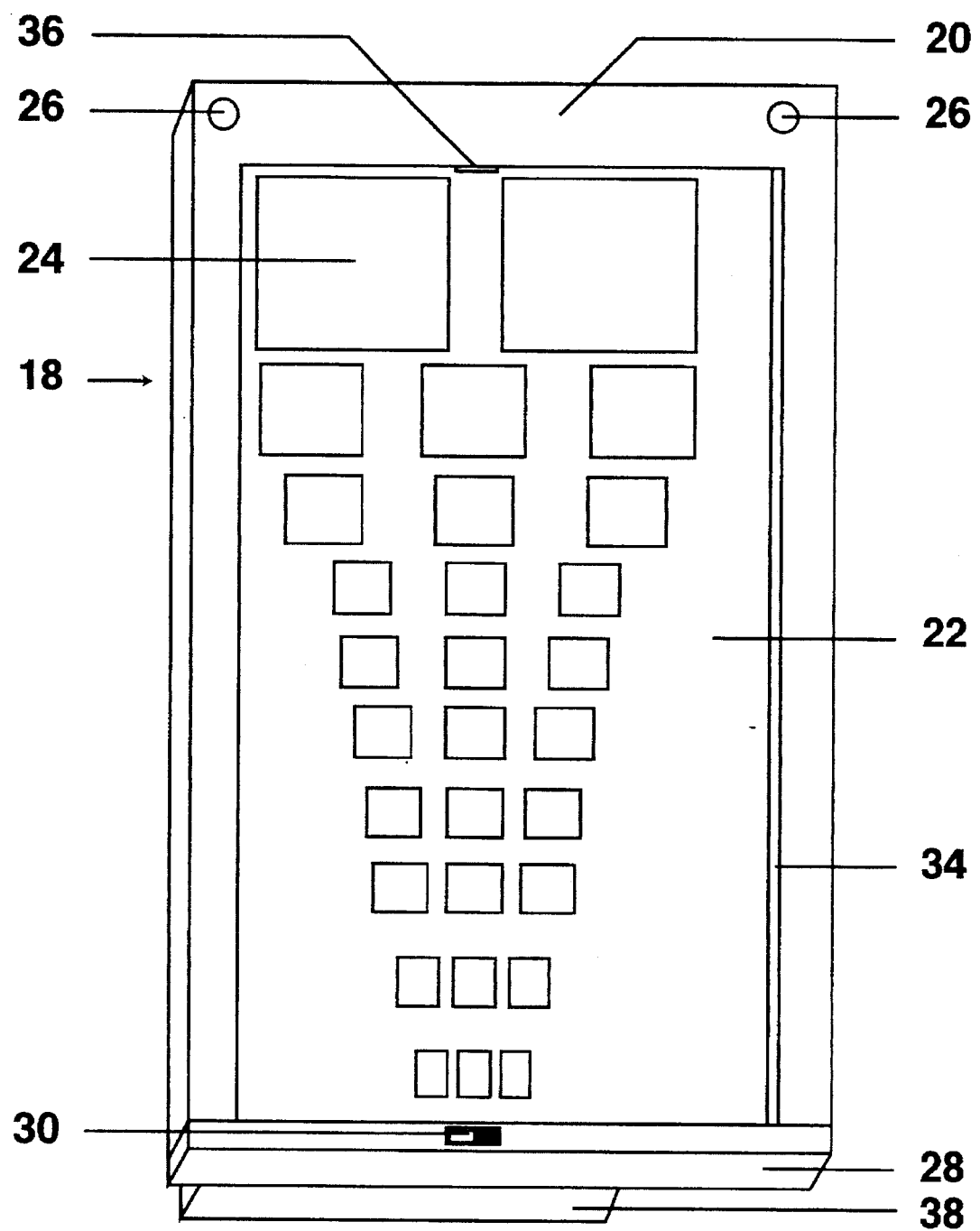
FIG. 1 is a front perspective view of the invention without a test card inserted.

The reference numerals utilized in the drawings are described below:

18 automated pocket-sized near vision tester
20 frame-like enclosure
22 printed circuit board
24 electroluminescent panels
26 enclosure securing holes
28 hinged lower border of enclosure 20
30 mechanical slide switch
32 translucent near vision test card
34 test card securing grooves
36 test card locator bar
37 horizontal cross-sectional line
38 battery holder
39 vertical cross-sectional line
40 near vision test objects
42 test card locator notch
44 test card securing holes
46 beveled test card securing pins
48 test card securing bar
50 test card securing springs
52 test card release button
54 protruding reading card rod
56 phoropter
57 test card securing apparatus
58 eye and ear examination unit
60 ophthalmoscope
61 otoscope
62 coiled power cord
63 test card securing prongs
64 "change row" pushbutton switch
66 "change column" pushbutton switch
68 "intensive care" pushbutton switch
70 "direction" pushbutton switch
72 sliding battery case cover
74 external power jack
76 power switch
78 Intel 8748H microcontroller
80 microprocessor crystal
82 power inverters
86 (a–c) PNP transistors
88 (a–j) NPN transistors
89 resistors, 2.2 Kohm
90 battery cell
94 microcontroller input ports
96 microcontroller output ports
100 DC to AC voltage inverter chip
102 inductor
104 output capacitor
106 control resistors
108 flat panel display
110 photocell
112 "randomize test objects" pushbutton switch
114 "change style of test objects" pushbutton switch
116 "change advanced vision test" pushbutton switch
117 "reference table" pushbutton switch
118 rear face LCD test indicator
120 switches
122 display interface
124 intensity control
130 light panel
134 light source
136 light gate

DETAILED DESCRIPTION OF THE INVENTION AND OF THE PREFERRED EMBODIMENTS

FIG. 1 is a front perspective view of the invention 18 without the translucent near vision test card 32 inserted. The automated pocket-sized near-vision tester is comprised of a frame-like enclosure 20 which houses a printed circuit board 22. Light sources 24 are mounted in rows and columns on the front face of the printed circuit board 22. The enclosure 20 is preferably manufactured from black plastic material, although other materials may be used. The printed circuit board 22 is preferably manufactured from glass epoxy material, although other insulating materials may be used. The light sources 24 are thin electroluminescent panels, in this case measuring about 0.012 inch in depth, and emitting a maximum white light of 80 foot lumens. The electroluminescent panels may be obtained from BKL, Inc., of King of Prussia, Pa. The panels consist of Kard-o-lite (TM) material embedded in a thin layer of transparent insulator and placed between a metal electrode and a transparent electrode. One hundred volts of alternating current is required to illuminate these particular panels. Of course, alternative light sources may be used, including light emitting diodes, fluorescent lamps, incandescent lamps, or other well known means of generating light.

The frame-like enclosure 20 has two securing holes 26, one in each upper corner. The lower border 28 of the enclosure 20 is hinged to allow access to a translucent near vision test card 32, shown in FIG. 2. When mechanical slide switch 30 is operated, the lower border 28 of the enclosure 20 can be rotated down allowing the easy insertion and removal of a translucent near vision test card 32 into test card securing grooves 34. These grooves 34 extend along the internal vertical edges of the enclosure 20 above the electroluminescent panels 24. Test card locator bar 36 is located on the internal upper edge of the enclosure 20. Battery holder 38 is seen protruding from the lower rear face of the enclosure 20. This embodiment of the invention measures about 6.5 inches high, 3.5 inches wide, and 0.75 inches deep.

Figure 2:
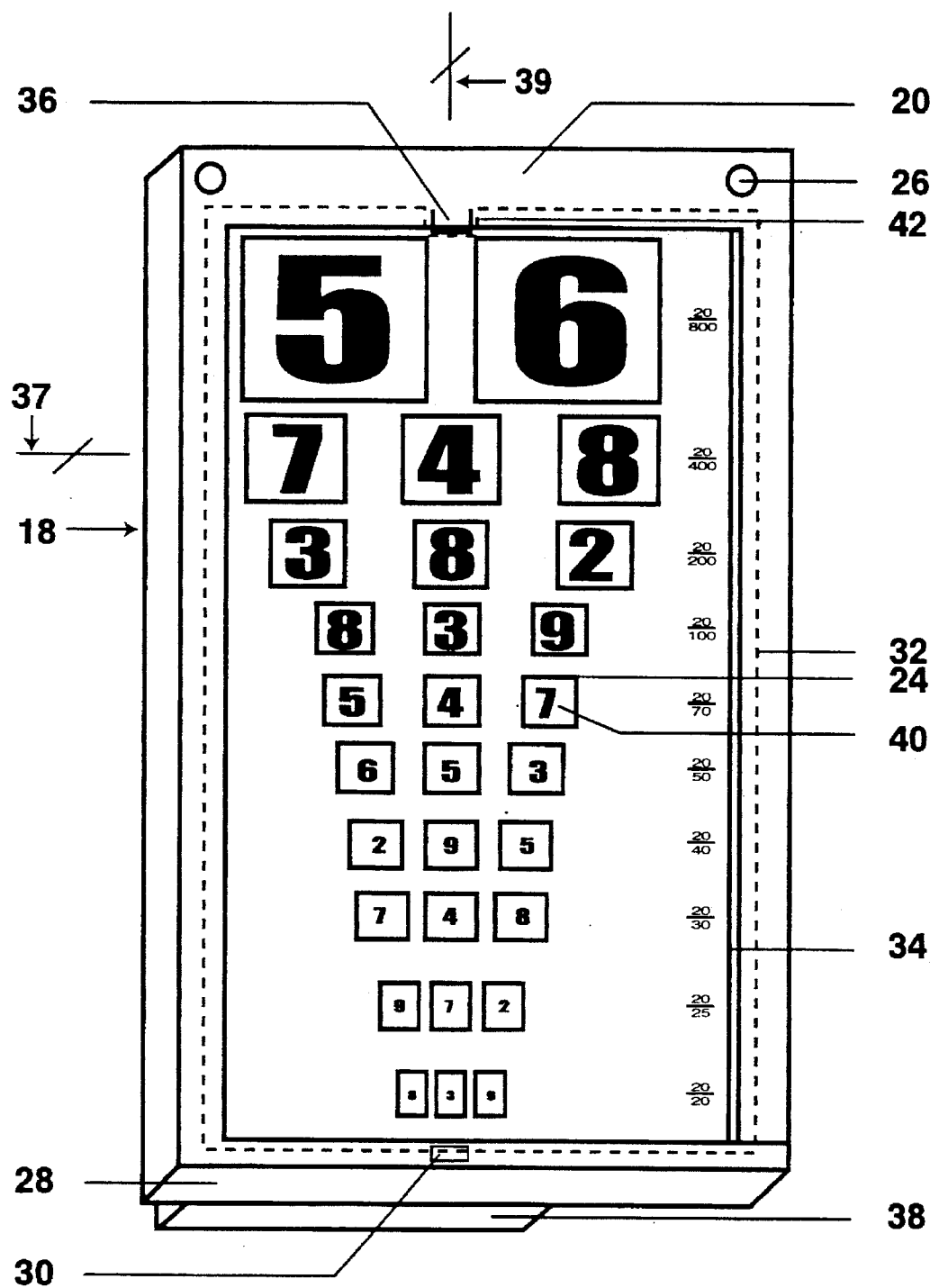
FIG. 2 is a front perspective view of the invention with a test card inserted.

FIG. 2 is a front perspective view of the invention 18 with a translucent near vision test card 32 inserted, thus forming the front face of the invention. The test card 32 is preferably composed of a translucent plastic material. On the test card are printed rows of black non-translucent or opaque vision test objects 40. Of course, near vision test objects may be laminated, bonded, stenciled, printed, or otherwise affixed to the test card. Different test cards 32 may have different types of test objects 40 such as numbers, letters, pictures, or various symbols, possibly using colors other than black. This enables the examiner to vary the near vision test to meet the cognitive demands of the patient by using different test cards. The test objects 40 are arranged so that the largest test objects 40 are in the top row of the card with progressively smaller test objects 40 arranged in rows proceeding down the test card 32. Test objects 40 within a given row are of the same size and correspond to a given level of visual acuity when held fourteen inches from the patient's eye being tested. A visual acuity of 20/40 means the person's eye being tested can see at twenty feet what the eye of a person with normal vision can see at forty feet. In other words, the larger the denominator in the visual acuity measurement, the worse the vision of the patient.

Precise alignment of the test card 32 in the enclosure 20 is required to position each test object 40 directly in front of its corresponding electroluminescent panel 24. As the test card is inserted into the upper aspect of grooves 34, locator notch 42 on the upper edge of the card 32 encounters locator bar 36. This lock and key mechanism prevents any horizontal movement of the test card 32. Closing lower hinged border 28 of the enclosure 20 prevents any vertical movement of the test card 32. Once test card 32 is secured in enclosure 20 in this way, the card's test objects 40 will remain centered in front of their corresponding electroluminescent panels 24.

FIG. 3 illustrates an alternative method for ensuring the proper positioning of the test card 32 in the enclosure 20. Instead of using a locator notch 42, two test card securing holes 44 are located near the upper edge of the test card 32. As the test card 32 is inserted into the upper aspect of grooves 34, the upper leading edge of the test card 32 encounters two beveled securing pins 46 which are mounted on test card securing bar 48. Two springs 50 are mounted between the securing bar 48 and the front surface of the printed circuit board 22. As the test card 32 is inserted, the springs 50 allow the beveled securing pins 46 to be depressed by the leading edge and upper rear surface of the test card 32. Once the upper beveled edges of the securing pins 46 encounter the securing holes 44, the spring mechanism (48, 50) elevates the securing pins 46 into the securing holes 44 thereby firmly securing the test card 32 in a precise location. To remove the test card 32, the hinged lower border 28 of the enclosure 20 is opened. The securing bar 48 is depressed manually by pressing down on test card release button 52. The test card 32 is then pulled out by grasping its lower edge. The ability to exchange different test cards 32 allows the examiner to rapidly modify the near vision test to meet the patient's cognitive abilities. Of course, there are many other methods of securing the test card 32 that are well known in the mechanical art. These other methods may not necessarily use a hinged enclosure 20, grooves 34, or the locking mechanisms described herein.

Figure 4:
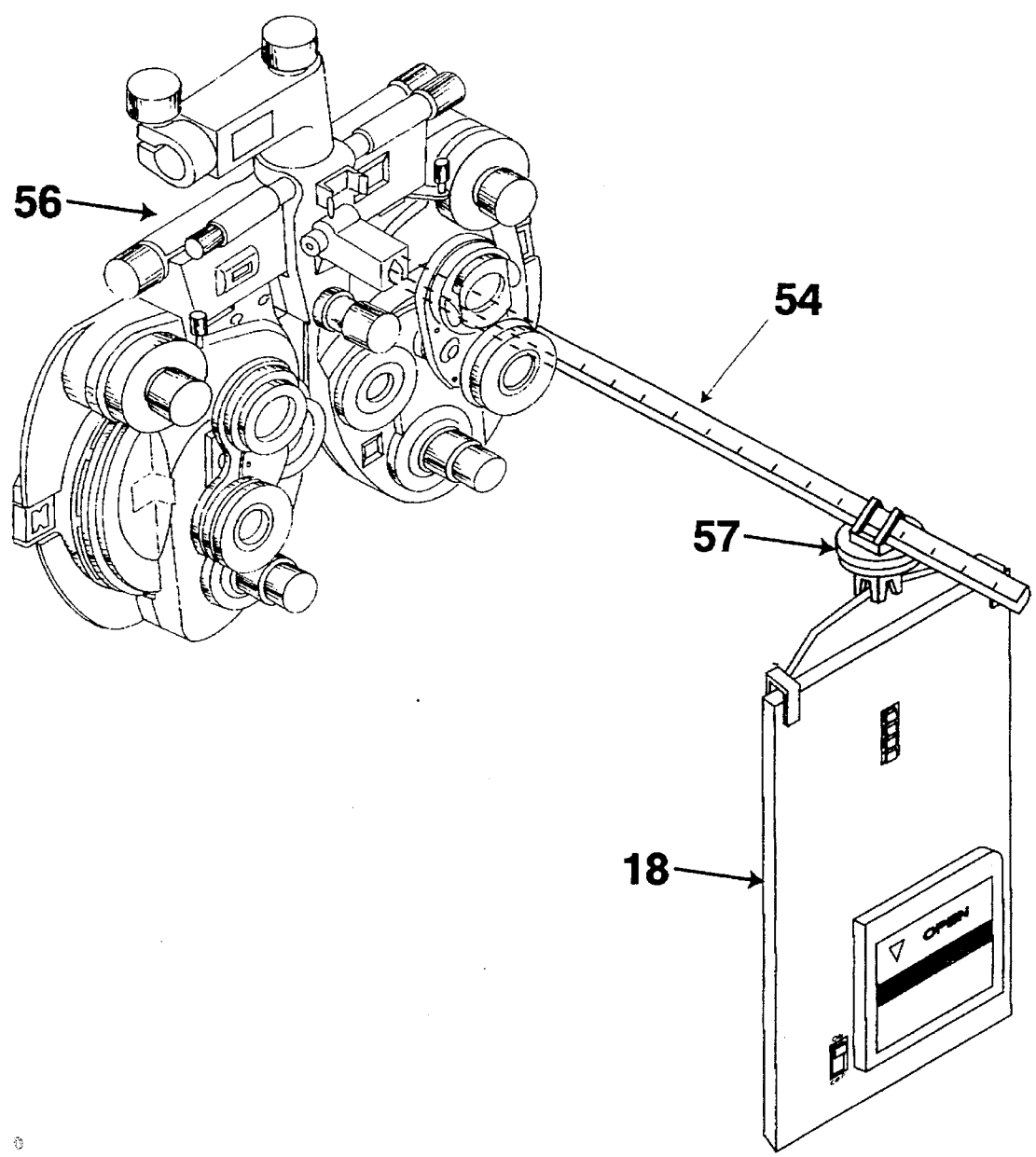
FIG. 4 illustrates the invention secured to the protruding reading card rod of a phoropter.
Figure 5:
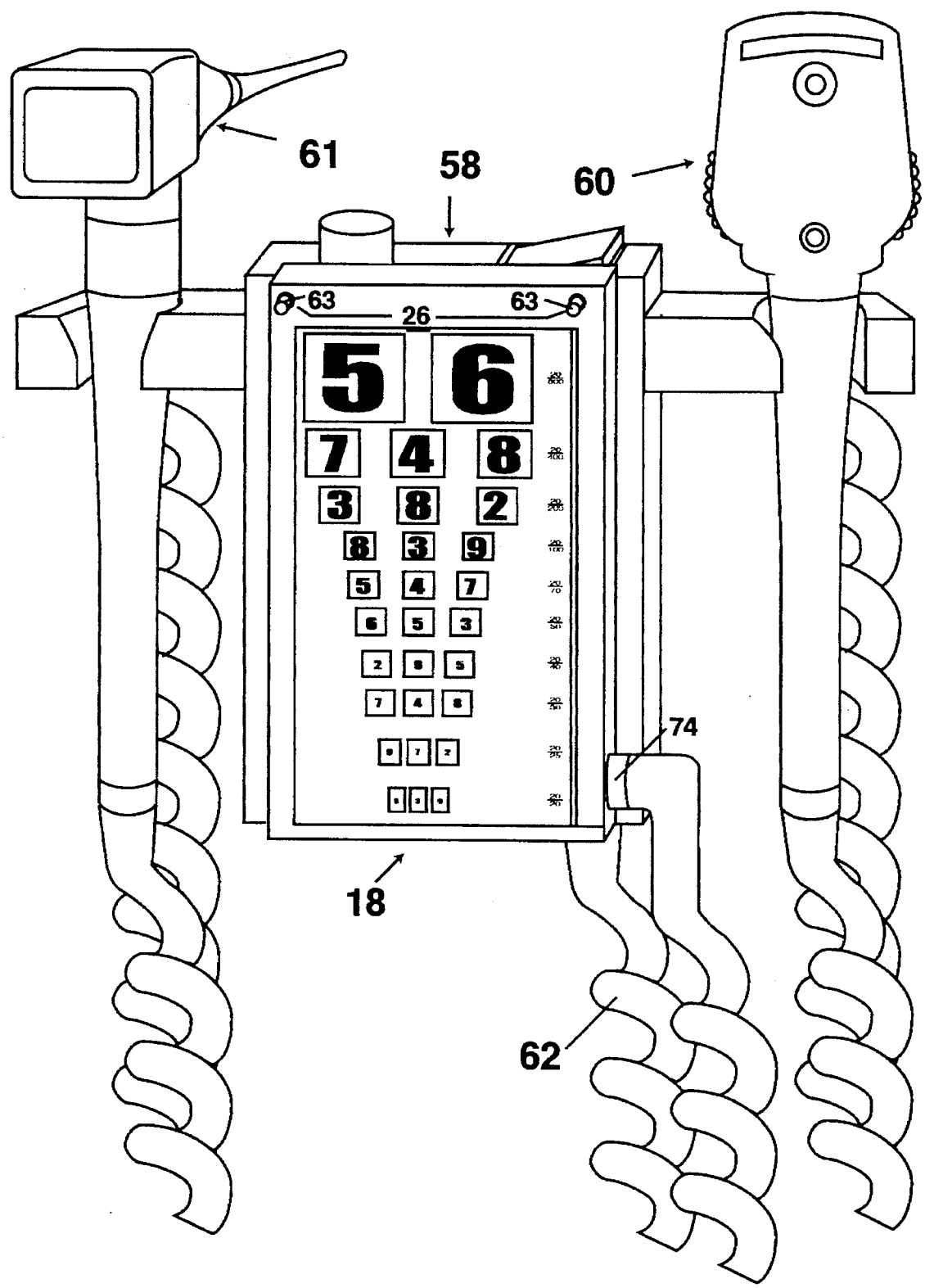
FIG. 5 illustrates the invention as part of an eye and ear examination unit.

As seen in FIGS. 4 and 5, the enclosure securing holes 26 enable the examiner to easily secure the invention 18 to other integrated eyecare equipment. In FIG. 4, the invention 18 is removably secured to the protruding reading card rod 54 of a phoropter 56 by means of a sliding test card securing apparatus 57. In FIG. 5, the invention 18 is removably secured to integrated eyecare equipment in the form of a wall-mounted or stand-mounted eye and ear examination unit 58 that houses examination devices such as an ophthalmoscope 60 and an otoscope 61. As an alternative to battery operation, the invention 18 may be connected via external power jack 74 to a coiled power cord 62 attached to the exam unit 58. When the invention 18 is lifted from attachment prongs 63, springs in the exam unit 58 move the prongs 63 upward against gravity, thereby connecting the power from the exam unit 58 through the power cord 62 to the invention 18. In a similar manner, the invention 18 may be removably secured to other integrated eyecare or healthcare equipment.

Figure 6:
FIG. 6 illustrates different styles of near vision test objects.

In FIG. 6, several different types of size 20/100 test objects 40 are pictured. From top to bottom are pictured numbers, letters, tumbling E's, Landolt rings, X's and O's, and children's pictures. These and other test objects 40 may be imprinted on or affixed to near vision test cards 32 used with the invention, or the test objects 40 may be displayed on flat panel displays.

Figure 7:
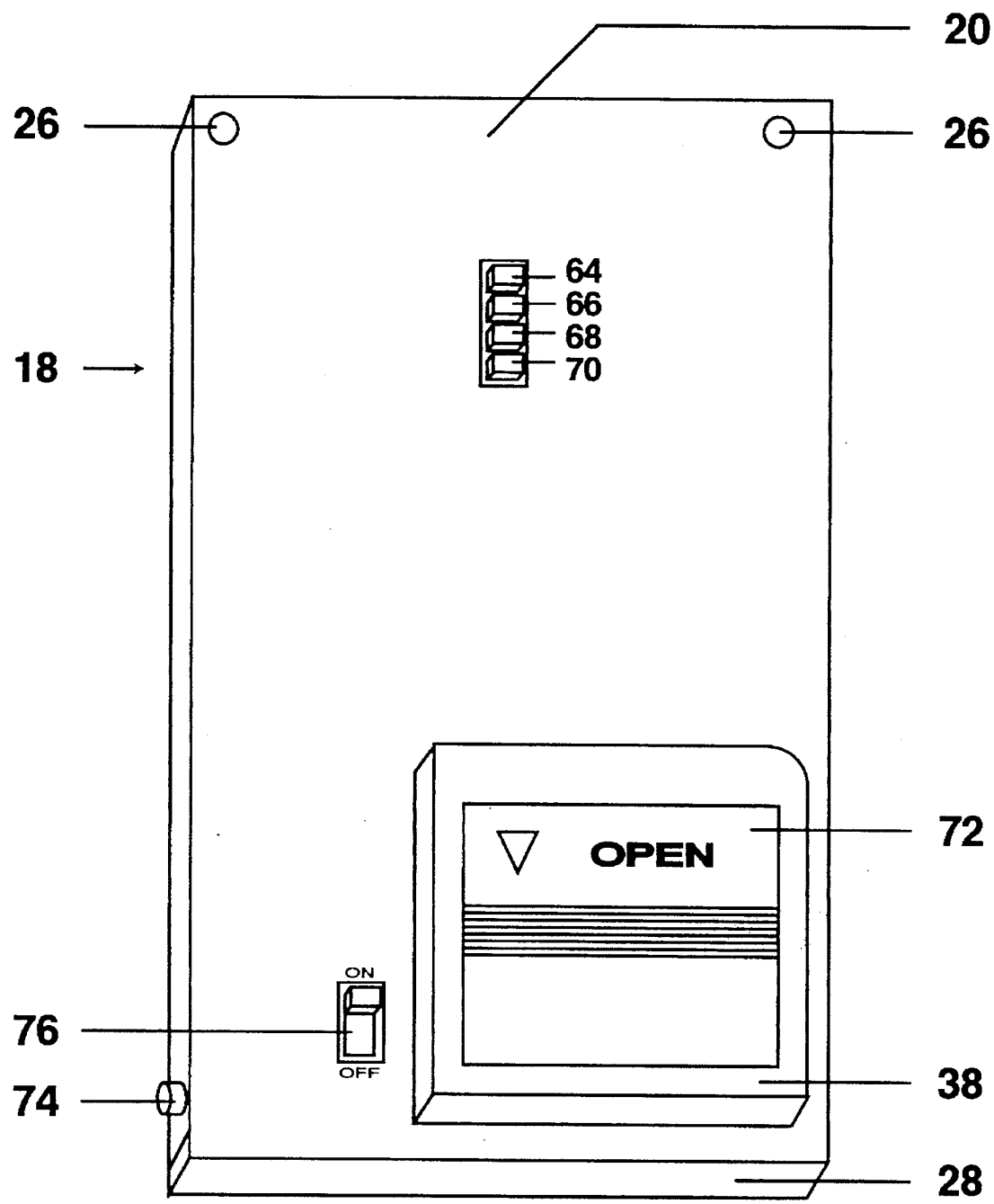
FIG. 7 is a rear perspective view of the invention.

In FIG. 7, a rear perspective view of the invention 18 is illustrated. Four pushbutton switches (64, 66, 68, 70) mounted near the center of the upper edge of the rear face of printed circuit board 22 are seen protruding from the rear face of the enclosure 20. Also seen in FIG. 7 are battery holder 38, sliding battery case cover 72, external power jack 74, power switch 76, and enclosure securing holes 26.

Figure 8:
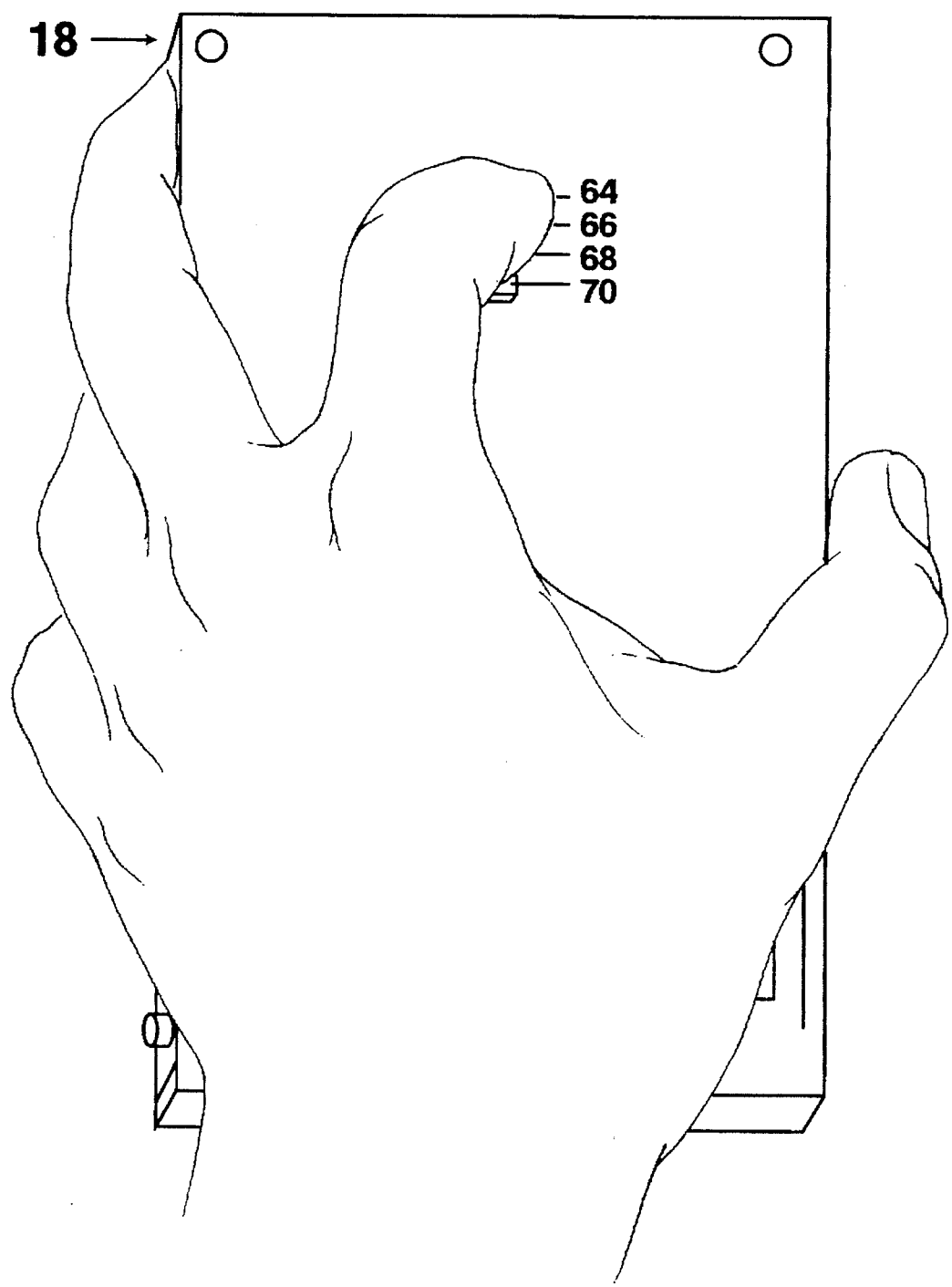
FIG. 8 is a rear perspective view of the invention being operated by the examiner.

As seen in FIG. 8, the pushbuttons (64, 66, 68, 70) are centered near the upper edge of the enclosure 20 for ease of operation with the index finger of the examiner's hand while the entire invention 18 is held with the thumb and other fingers of the same hand. In this way, the examiner may operate the invention 18 with either hand, keeping the other hand free for performing necessary tasks during the near vision test.

Figure 9:
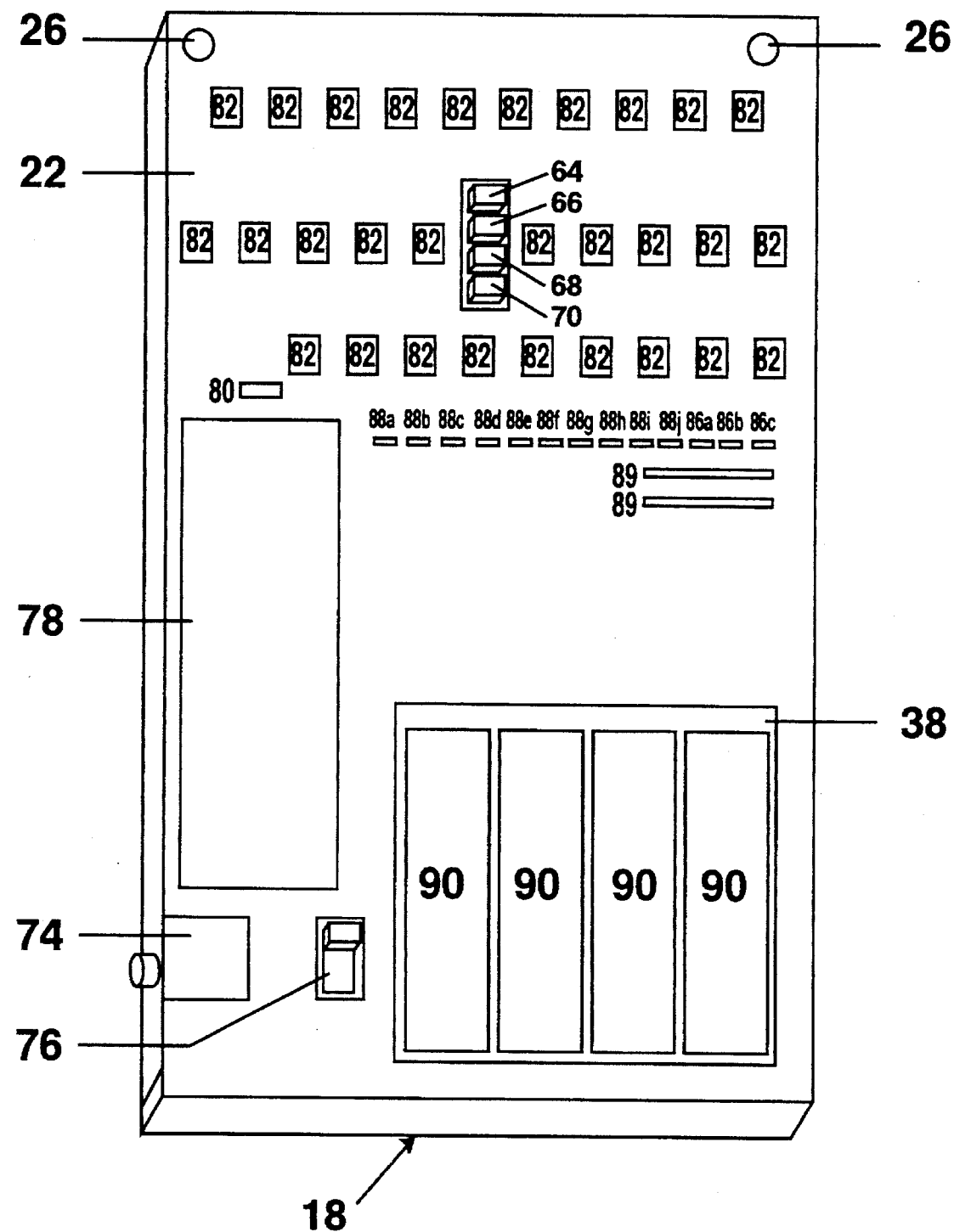
FIG. 9 is a rear elevation view of the printed circuit board in the invention with the rear face of the enclosure removed.

In FIG. 9, the rear surface of the enclosure 20 has been removed, thereby exposing the rear surface of the printed circuit board 22. The four pushbutton switches (64, 66, 68, 70) provide inputs to a microcontroller 78. The microcontroller is an Intel 8748H, programmable logic, 8 bit parallel computer. The following components mounted on the rear face of the printed circuit board 22 are also seen in FIG. 9: external power jack 74, power switch 76, microprocessor crystal 80, twenty-nine power inverters 82, three PNP transistors 86(a–c), ten NPN transistors 88(a–j), two 2.2 Kohm resistor packs 89, and battery holder 38 with four interchangeable batteries 90 inserted. Potential battery 90 options include alkaline, lithium, and nickel-cadmium rechargeable, as well as other batteries known in the field. Of course, other types of microcontrollers may be used, or alternatively, gate arrays or other types of logic circuitry may be used in place of a microcontroller.

Figure 10:
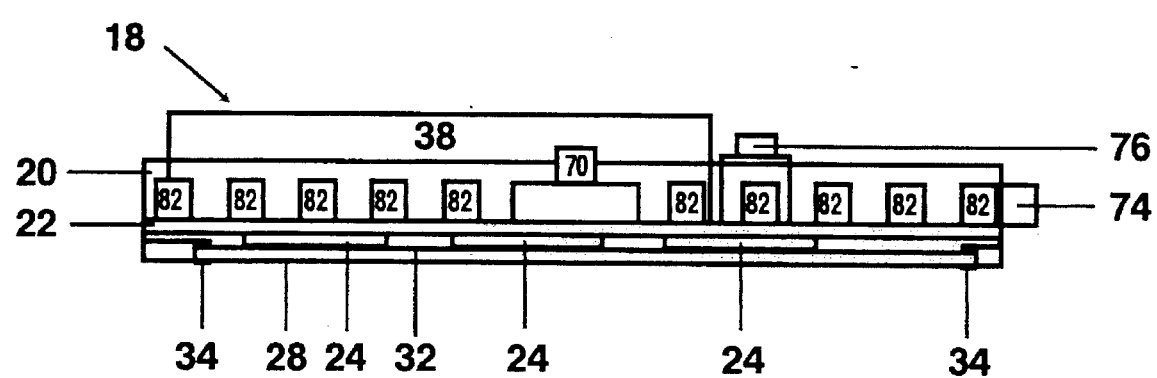
FIG. 10 is a horizontal cross-sectional view of the invention corresponding to cross-section line 37 of FIG. 2.

FIG. 10 is a horizontal cross-sectional view of the invention 18 corresponding to cross-sectional line 37 of FIG. 2.

Figure 11:
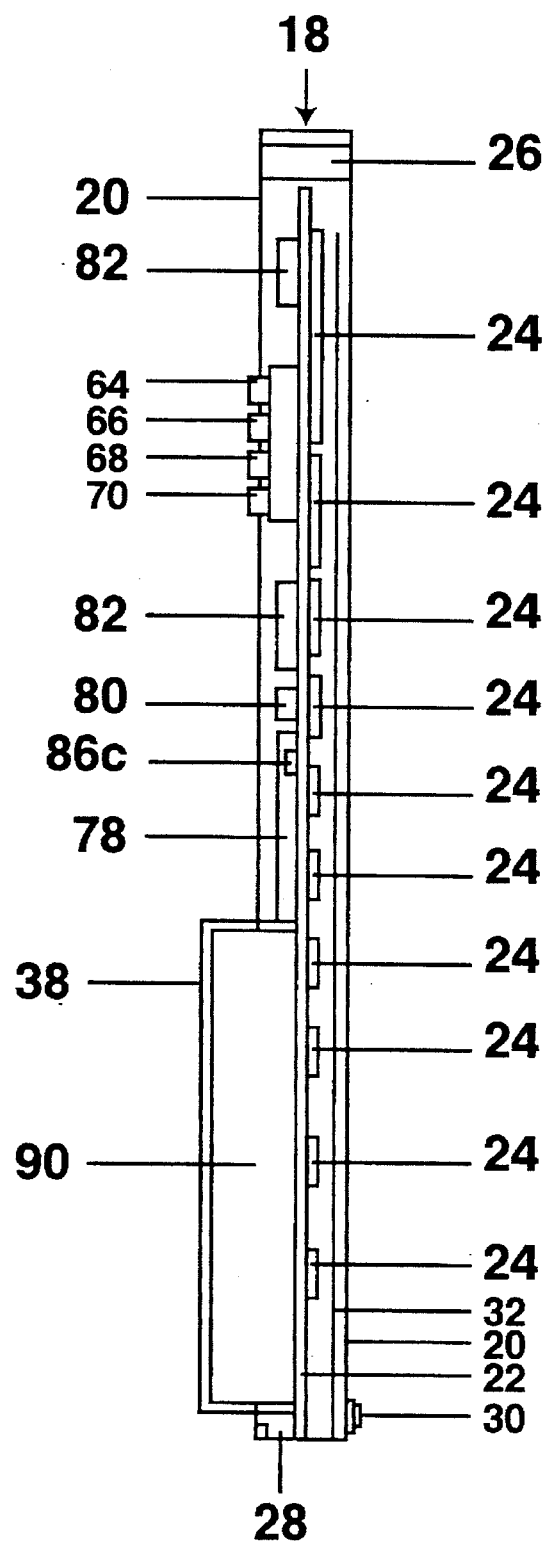
FIG. 11 is a vertical cross-sectional view of the invention corresponding to cross-section line 39 of FIG. 2.

FIG. 11 is a vertical cross-sectional view of the invention 18 corresponding to cross-sectional line 39 of FIG. 2.

Figure 12:
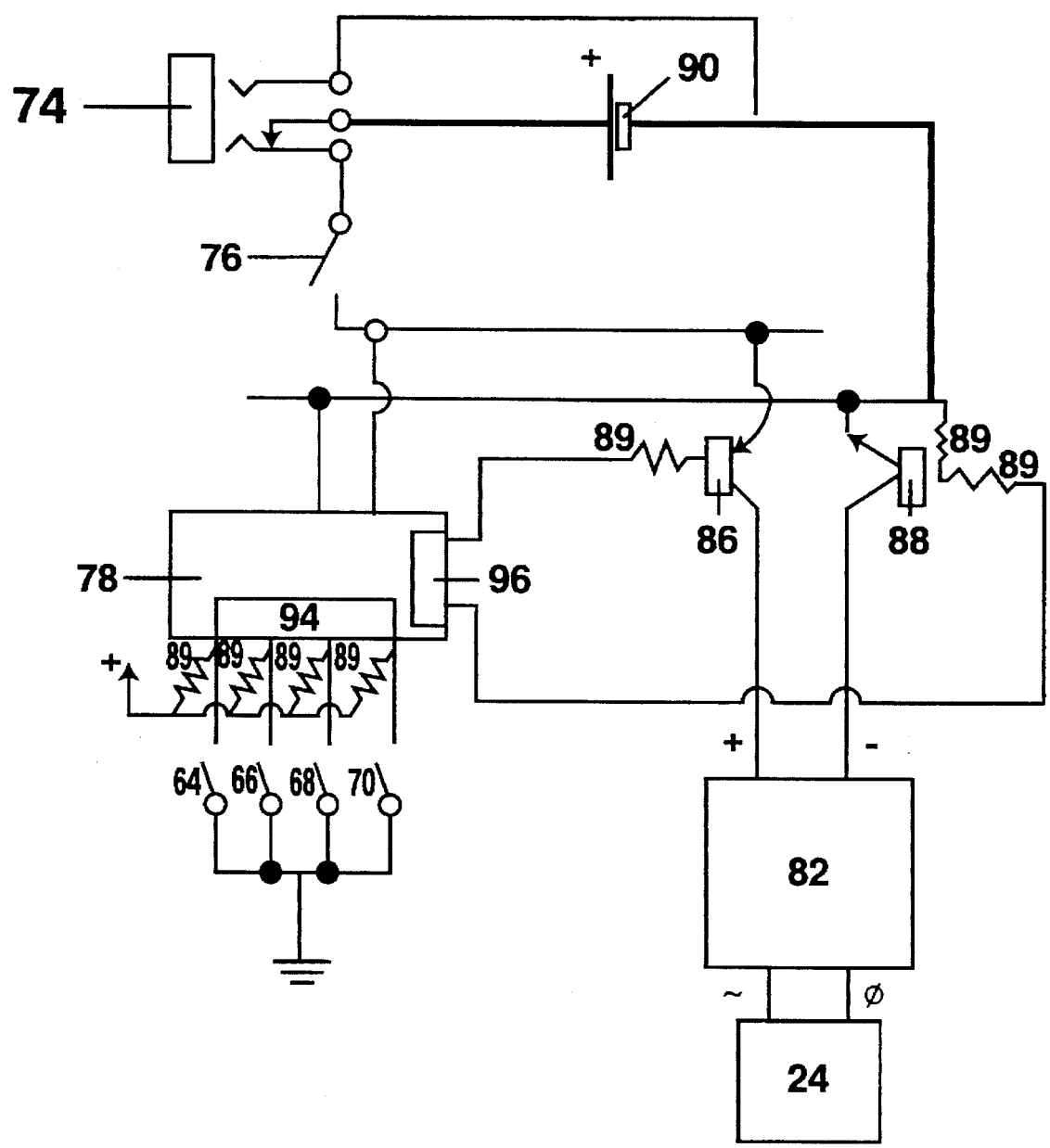
FIG. 12 is a schematic of the DC and AC electrical distribution and switching circuit of the invention.

In FIG. 12, the DC (direct current) and AC (alternating current) electrical distribution and switching circuitry of the invention 18 is illustrated schematically. For simplicity, circuitry to just one electroluminescem panel 24 is shown. Activation of the power switch 76 connects the DC battery source 90 to the microcontroller 78 and also to the emitters of PNP transistors 86(a–c), thereby turning on the invention 18. Activation of power switch 76 also connects the emitters of NPN transistors 88(a–j) to ground. As an alternative to battery power 90, an external power source may be connected via external power jack 74. When external power jack 74 is in use, the battery 90 is automatically disconnected from the circuitry. Microcontroller input ports 94 are connected to the four pushbuttons: "change row" 64, "change column" 66, "intensive care" 68, and "direction" 70. A 2.2 Kohm pull-up resistor 89 is connected between each pushbutton (64, 66, 68, 70) and the five volt supply to allow for correct electrical operation of the microcontroller 78. Microcomroller output ports 96 are connected via 2.2 Kohm resistors 89 to the bases of PNP transistors 86(a–c) and NPN transistors 88(a–j). On their input sides, each power inverter 82 is connected to one PNP transistor 86(a–c) and one NPN transistor 88(a–j). Each NPN transistor 88(a–j) has a 2.2 Kohm resistor connected between its base and ground. The output of each power inverter 82 is connected to one electroluminescent panel 24. When specific pushbuttons (64, 66, 68, 70) are operated by the examiner, the microcomroller 78 generates signals to a specific combination of PNP 86(a–c) and NPN 88(a–j) transistors, thereby activating a specific combination of power inverters 82. The power inverters 82 convert the DC output of the power source (90 or 74) to an AC output and connect that AC output to the corresponding electroluminescent panels 24, thereby activating or energizing the electroluminescent panels 24 and retroilluminating particular near vision test objects 40.

Figure 13:
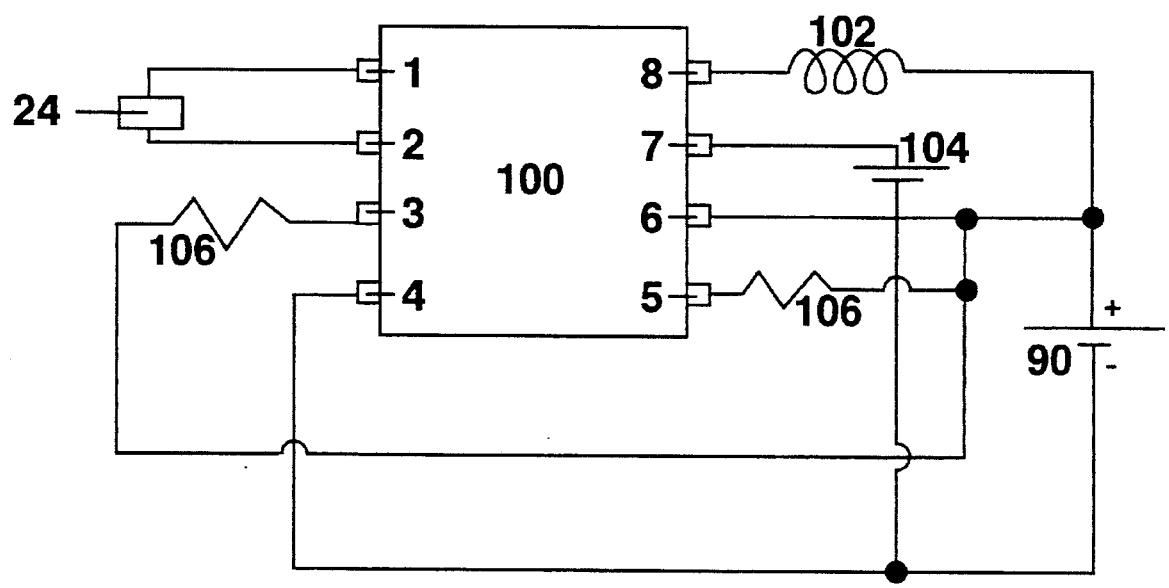
FIG. 13 is a schematic of one of the power inverter circuits.

FIG. 13 is a schematic of one of the power inverters 82 which consists of a DC to AC inverter chip 100, an inductor 102, a capacitor 104, and two resistors 106. A DC voltage fed into inputs 6 and 4 of the inverter chip 100 causes an AC output to be delivered on pins 1 and 2 of inverter chip 100 thereby activating the electroluminescent panel 24 that is connected to pins 1 and 2 of inverter chip 100.

Figure 14:
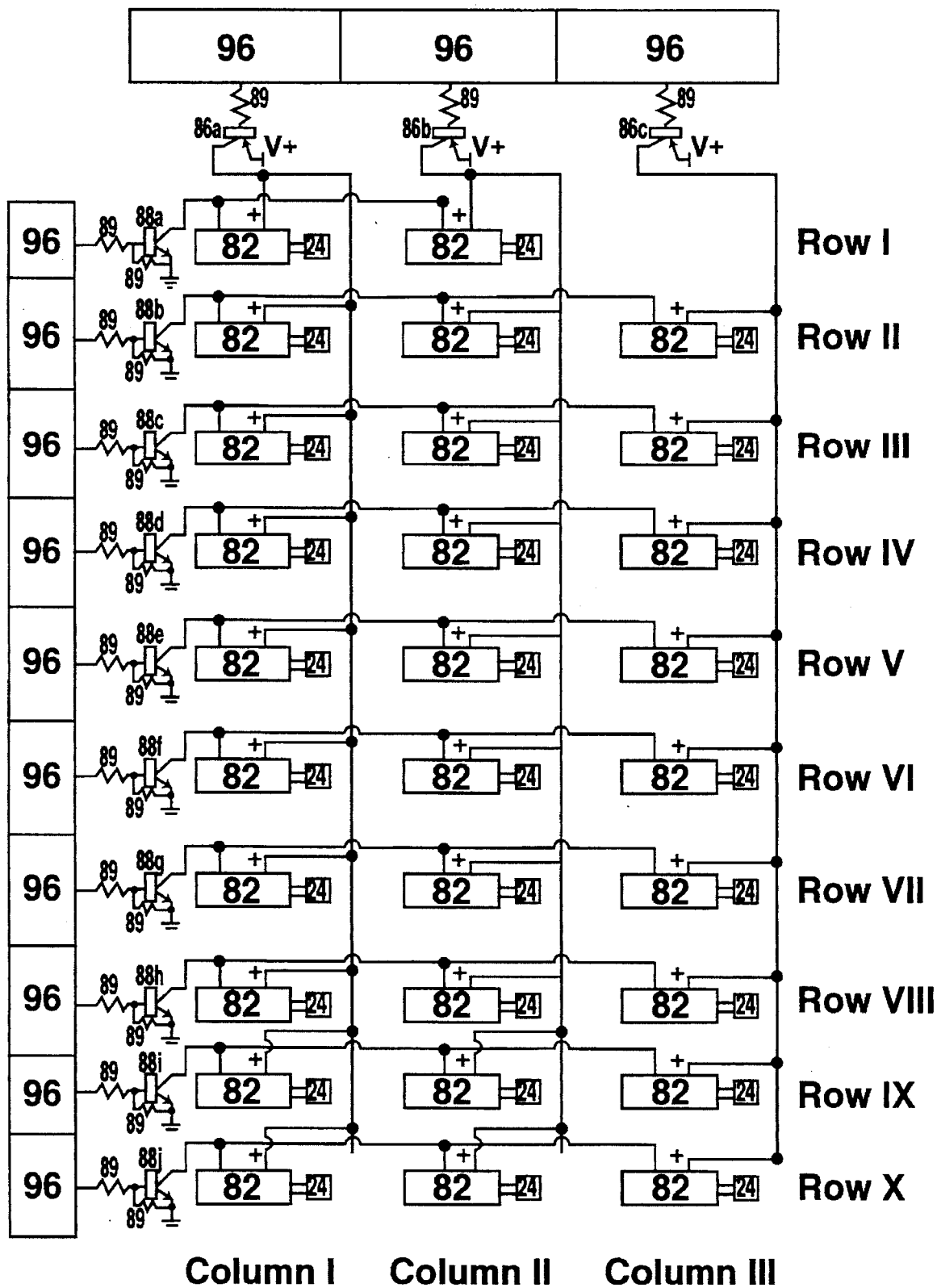
FIG. 14 is a schematic of the electrical switching circuit of the power inverters and electroluminescent panels.

In FIG. 14, the electrical circuit of all twenty-nine power inverters 82 and their corresponding electroluminescent panels 24 is illustrated schematically. The electroluminescent panels 24 are arranged in ten rows, labeled "Row I" through "Row X," and in three columns, labeled "Column i," "Column ii," and "Column iii." When the invention 18 is initially turned on, none of the electroluminescent panels 24 are illuminated. As stated earlier, different combinations of electroluminescent panels 24 may be illuminated by different combinations of signals coming from the output ports 96 of the microcomroller 78 in response to the operation of pushbuttons switches 64, 66, 68, or 70 by the examiner. When only one electroluminescent panel 24 is to be illuminated, the microcomroller 78 connects a ground signal from one of its output ports 96 through one of three 2.2 Kohm resistors 89 to the base of one of three PNP transistors 86(a–c). This causes voltage from the power source (90 or 74) to be connected to a column of power inverters 82. Simultaneously, the microcontroller 78 sends a five volt signal from another of its output ports 96 through one of ten 2.2 Kohm resistors 89 to the corresponding base of one of ten NPN transistors 88(a–j), thereby connecting to ground a row of three power inverters 82. This combination of signals activates the power inverter 82 that receives both a voltage source from a PNP transistor 86(a–c) and a ground from an NPN transistor 88(a–j). Once a power inverter 82 is activated, it provides AC power to its corresponding electroluminescent panel 24, thereby activating it and causing the panel to emit light.

In a similar manner, the microcontroller may selectively activate a row of electroluminescent panels 24, thereby selectively retroilluminating a row of near vision test objects 40. The microcontroller 78 sends a ground signal from three of its output ports 96 to each of three PNP transistors 86(a–c), thereby connecting voltage from the power source (90 or 74) to all three columns of power inverters 82. Simultaneously, the microcomroller 78 sends a five volt signal from another of its output ports 96 to one of ten NPN transistors 88(a–j), thereby connecting a ground to one row of power inverters 82. This activates the row of power inverters 82 that receives both a voltage source from the three PNP transistors 86(a–c) and a ground from an NPN transistor 88(a–j). All of the electroluminescent panels 24 may be activated at once if the microcontroller 78 sends simultaneous ground signals to all three PNP transistors 86(a–c) and sends five volt signals to all ten NPN transistors 88(a–j).

The examiner operates the pushbuttons as a means for controlling the selective retroillumination of near vision test objects 40. In doing so, the examiner may select one of a number of operational modes, such as "change row," "change column," "intensive care," and "all." Considering FIGS. 12–14, when the examiner presses the "change row" pushbutton 64 as his or her first selection, the test apparatus is placed in the "change row" mode, and the two test objects of the top row (Row I/Columns i and ii) are selectively retroilluminated by means of the circuitry described above. Note that in this particular embodiment of the invention 18, there are only two columns in Row I, and the other nine rows contain three columns each. Pressing the "change row" button 64 a second time turns off illumination of the two test objects 40 in Row I and illuminates the three test objects 40 of Row II. Likewise, the other rows of test objects 40 may be illuminated by successively pressing the "change row" button 64.

Should the examiner desire to begin the vision test on the bottom row (Row X) of smallest test objects 40 and proceed up the test card to larger test objects 40, the "change row" button 64 must first be pressed after the power has been turned on, thereby illuminating Row I. The "direction" 70 button is then pressed turning off Row I and illuminating Row X. Each successive press of the "change row" button 64 will turn off the previously illuminated row and illuminate the next row proceeding up the test card 32. If the test is proceeding down the test card 32 and Row X is illuminated, the next press of the "change row" button 64 turns off Row X and illuminates Row I. If the test is proceeding up the test card 32 and Row I is illuminated, the next press of the "change row" button 64 turns off Row I and illuminates Row X.

Once the patient encounters difficulty with a given row of illuminated test objects 40, the "change column" pushbutton 66 may be used to place the test apparatus in the "change column" mode and selectively illuminate individual test objects 40 in that row. For example, if the patient first encounters difficulty in reading the illuminated test objects 40 on Row VII, the "change column" pushbutton 66 may be pressed to turn off Row VII/Columns ii and iii while keeping the individual test object 40 in Row VII/Column i illuminated. Pressing "change column" 66 a second time turns off Row VII/Column i and illuminates Row VII/Column ii, and pressing "change column" 66 a third time turns off Row VII/Column ii and illuminates Row VII/Column iii. When the last test object 40 in a row is individually illuminated, pressing the "change column" button 66 again will turn off illumination of that test object and illuminate the first test object 40 in the next row. If the "change row" button 64 is pushed while an individual test object 40 is illuminated, the apparatus will be placed in the "change row" mode, and all test objects 40 in the same row will be illuminated. Pressing "change column" 66 first after power has been turned on begins the test by illuminating Row I/Column i.

If the examiner wants to reverse the direction of successive illumination of test objects 40, he or she can simply press the "direction" button 70. If the test is proceeding in the "change column" mode in a left to right direction, pressing the "direction" button 70 will turn off the illuminated test object and illuminate the test object 40 immediately to its left. Each successive press of the "change column" button 60 will turn off the illuminated test object 40 and illuminate the test object in the next column in a right to left direction. If the test is proceeding in the "change row" mode in an up to down fashion, pressing the "direction" button 70 will turn off the illuminated row and illuminate the row immediately above it. Each successive press of the "change row" button will turn off the illuminated row and illuminate the next row in an upward direction.

Pressing the "intensive care" pushbutton 70 first after power has been turned on places the apparatus in the "intensive care" mode and illuminates a single number in the top row of test objects (always a 2, 3, 4, or 5). Pressing the "intensive care" button 70 a second time will turn off the illuminated number in Row I and illuminate a single number in Row II (2, 3, 4, or 5). Likewise, successive presses of the "intensive care" button 70 allow the examiner to direct the intensive care unit patient's visual attention down the test card. Individually illuminated numbers (2, 3, 4, or 5) are used so that mechanically-ventilated or otherwise speech-impaired patients may use their fingers or eye blinks to signal a response. As depicted in FIG. 2, only one test object in each row must be a 2, 3, 4, or 5 as only one intensive care test position per row is programmed into the microcontroller 78. Should the examiner desire to start on the bottom row (Row X) of smallest test objects 40 and proceed up the test card 32, the "intensive care" button 70 should be pressed first after the power has been turned on, thereby illuminating a single number (2, 3, 4, or 5) in Row I. The "direction" button 70 is then pressed turning off the illuminated number (2, 3, 4, or 5) in Row I and illuminating a single number (2, 3, 4, or 5) in Row X. Then, each successive press of the "intensive care" button 70 will turn off the illuminated number (2, 3, 4, or 5) and illuminate a number (2, 3, 4, or 5) in the next row proceeding up the test card 32.

If the patient demonstrates sufficient cognitive abilities, the examiner may simply press the "intensive care" button 68 and "direction" 70 button simultaneously, which will place the apparatus in the "all" mode and illuminate all test objects 40. While all test objects 40 are illuminated, the examiner may then ask the patient to read the smallest row of test objects 40 within the patient's capability.

As an option, the front or rear face of the invention may contain LEDs or other display means for indicating the current operational mode of the invention, such as "change row," "change columns," "intensive care," or "all." In addition, the "direction" of operation, such as left/right or up/down may be indicated along with the operational mode. The rear face of the invention also may contain a means for indicating to the examiner which of the near vision test objects 40 are selectively retroilluminated. This may be accomplished by attaching to the rear face of the device a miniaturized replica of the near vision test card 32, which would be selectively retroilluminated by LEDs or other illumination devices that are selectively activated in the manner corresponding to the selective activation of the electroluminescent panels 24. In this manner, an examiner would be able to look at the rear panel of the device and determine which near vision test objects 40 are illuminated on the from of the device.

OTHER EMBODIMENTS

Figure 15:
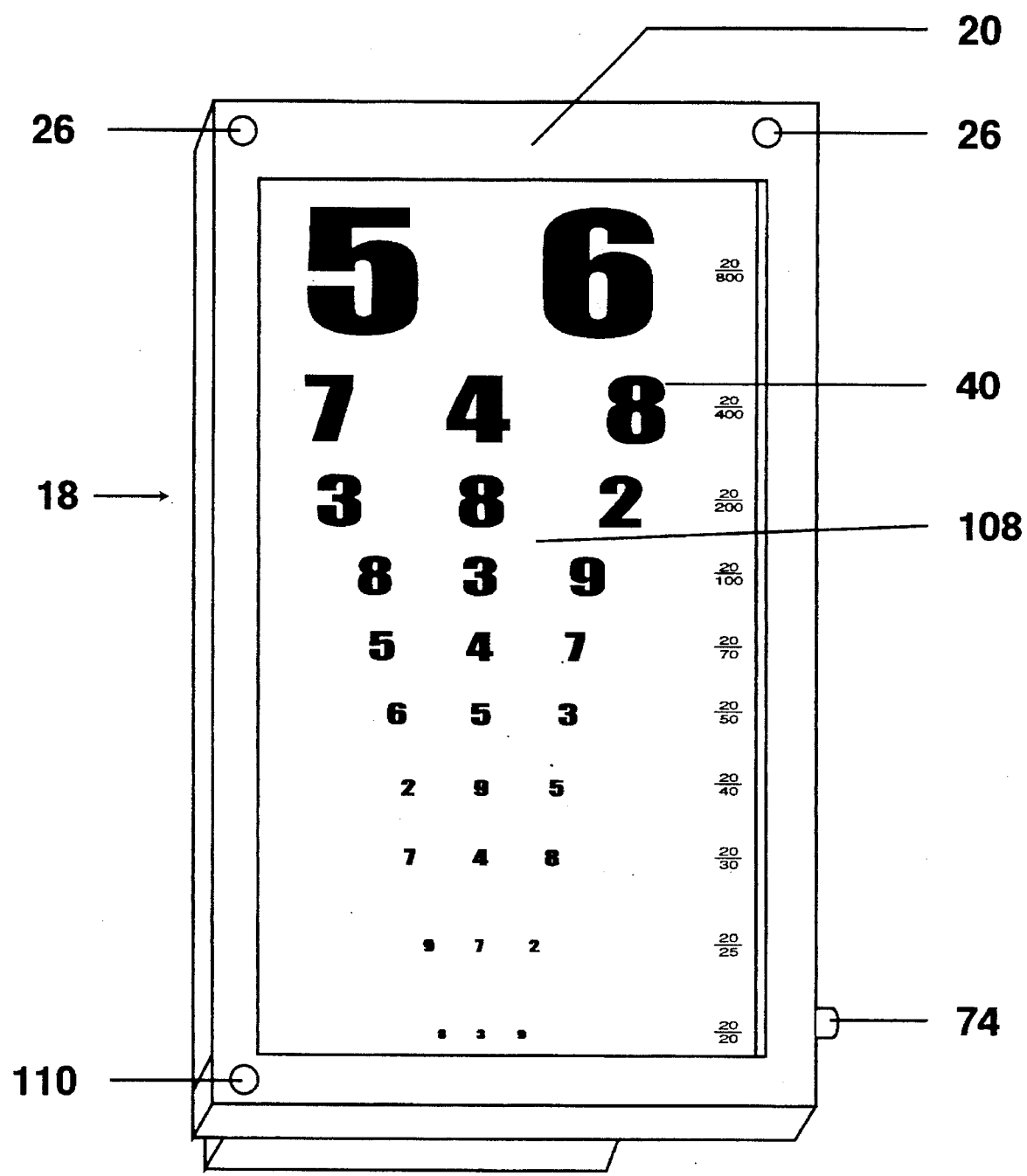
FIG. 15 is a front elevation view of an alternative embodiment of the invention with a flat panel display.

FIG. 15 illustrates an alternative embodiment of the invention 18 that uses an illuminated flat panel display 108 in place of the interchangeable near vision test card 32. Alternative forms of the flat panel display 108 include a liquid crystal display, plasma display, ferro-electric display, thin film transistor display, and similar displays that are known or may become known in the art. The flat panel display 108 may be color or black and white, depending on the needs of the examiner. The flat panel display 108 may be backlighted, as with a liquid crystal display, or it may generate its own illumination, as with an electroluminescent display or a thin film transistor display. The flat panel display 108 is mounted in enclosure 20 on or above the front face of printed circuit board 22. The flat panel display 108 is capable of displaying randomized vision test objects 40 of different styles, such as those shown in FIG. 6, under the control of a microcontroller 78. The test objects are stored in memory which is part of or accessible to the microcontroller 78.

An auto-intensity adjustment mechanism can be used to provide a constant degree of contrast illumination on the front face of the flat panel display 108. A photocell 110 indicates the amount of incident illumination that strikes the front face of the flat panel display 108 from surrounding light sources. The microcontroller 78 monitors the incident illumination through the photocell 110, and adjusts the illumination of the displayed vision test objects 40 accordingly to maintain a constant degree of contrast illumination between the test objects 40 and the incident illumination striking the front of the flat panel display 108.

FIG. 16 illustrates several different advanced vision testing options available in a flat panel display embodiment of the invention. Standardized color test plates, such as those known as "HRR," may be generated by the microcontroller 78 and displayed on the flat panel display 108 to test the patient's color vision. A circular white test panel (fixation spot) may be used to test ocular motility or eye muscle imbalance (strabismus). A circular red test panel may be displayed to test for color desaturation. A Worth four dot test panel may be displayed to further study strabismus findings. An Amsler grid may be displayed to test for image distortion (metamorphopsia) or blind spots in the central visual field (scotomas). Contrast sensitivity test panels may be displayed to determine contrast visual acuity. An optokinetic drum simulator may be displayed to test for functional visual loss or visual loss secondary to cognitive impairment. Movement of the black and white stripes alternates between a right to left direction for ten seconds then a left to right direction for ten seconds. Dynamic visual activity may be tested by displaying a motion picture sequence, such as a motion picture of a young girl pulling a wagon through the gate of a picket fence.

FIG. 17 illustrates a table of ophthalmologic abbreviations that may be displayed on the flat panel display 108. These abbreviations are frequently used by eyecare professionals to describe ocular history and physical examination in the medical record. This table also would serve as a readily available reference to other health professionals, who frequently have difficulty understanding the abbreviations in medical records prepared by eyecare professionals.

Figure 18:
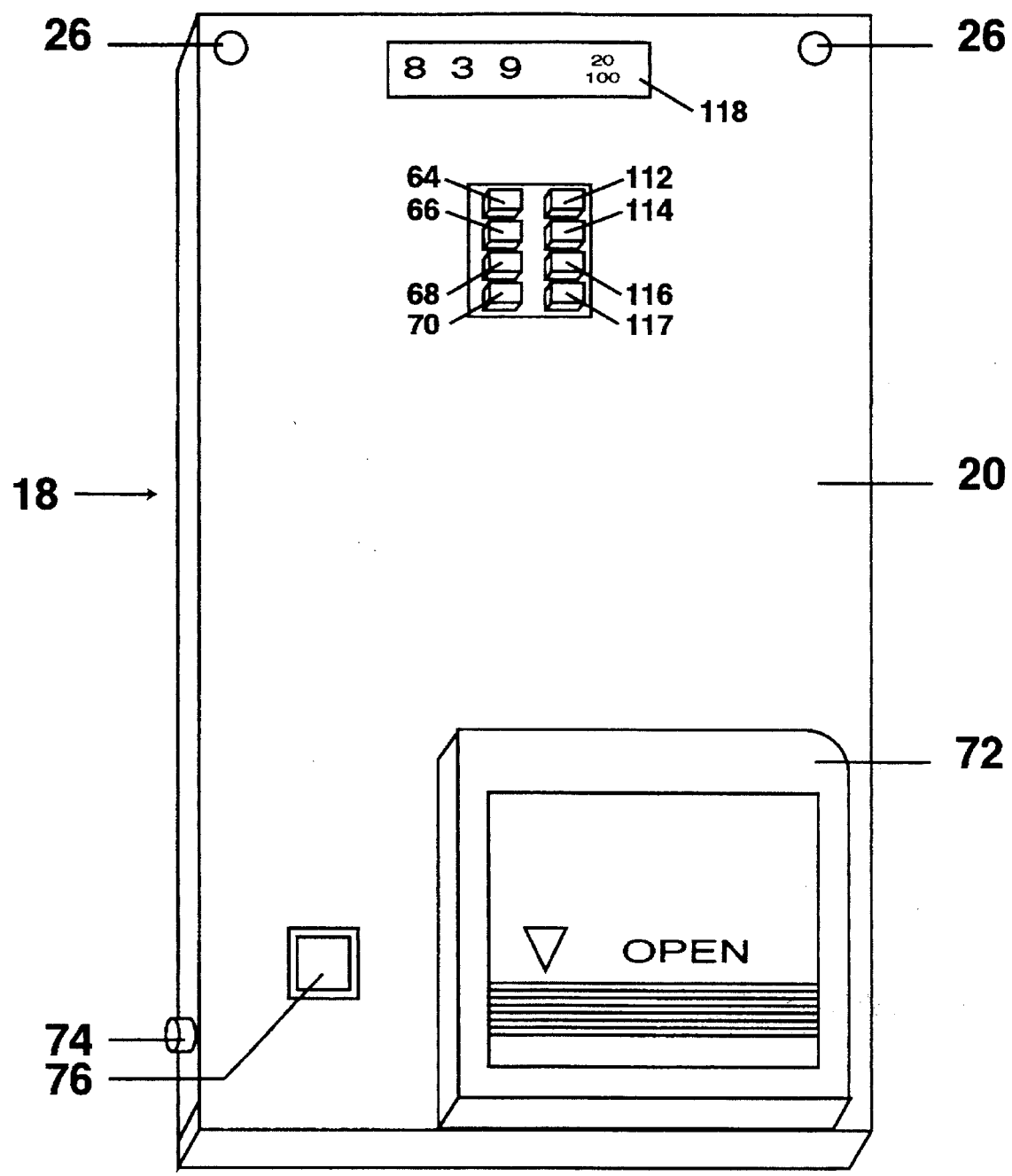
FIG. 18 is a rear elevation view of a flat panel display embodiment of the invention.

FIG. 18 is a rear elevation view of a flat panel display embodiment of the invention. The flat panel display 108 may be controlled by the microcontroller 78, as is well known in the art. Additional operational modes and options may be selected by the examiner using pushbuttons 112, 114, 116, and 117, which optionally may be added to the near vision test apparatus. For example, by operating "change advanced vision test" pushbutton 116, the examiner may sequentially display the different advanced vision tests shown in FIG. 16. Operation of "reference table" pushbutton 117 allows the examiner to display the table of abbreviations shown in FIG. 17, as well as other reference tables. In addition to selecting the operational modes of "change advanced vision test" and "reference table," switches may be used to select various options within the operational modes, such as "randomize test objects" and "change style of test objects." When the examiner presses the "randomize test objects" pushbutton 112, the near vision test objects 40 on the flat panel display 108 are rearranged or changed to new randomized vision test objects 40 of the same style. Operation of "change style of test objects" pushbutton 114 by the examiner changes the vision test objects 40 to a different style of vision test objects 40, such as the styles shown in FIG. 6.

Operation of pushbuttons 64, 66, 68, and 70 allows for selective display of vision test objects 40 in the same manner as in the embodiment of the invention that uses electroluminescent panels 24 and interchangeable near vision test cards 32. A small LCD panel 118 located above the pushbuttons may be used to indicate what is being displayed on the front face of the apparatus, in case the examiner is unable to view the front face of the test apparatus by standing to the side of the patient during the vision test. In addition, the current operational mode and options may be displayed in a similar fashion on the rear of the device, or on the flat panel display 108.

FIG. 19 illustrates a smaller embodiment of the invention 18 with a smaller flat panel display 108 that displays fewer rows of near vision test objects 40 than in the full-sized embodiment. This smaller embodiment is lightweight and easy to carry, and it is less expensive than the larger embodiments, because it utilizes a smaller flat panel display.

The smaller embodiment may display only one row at a time, as shown in FIGS. 19a, 19b, and 19c, or it may display several rows at a time, depending on the size of the test objects 40 and the size of the flat panel display 108. This smaller version of the invention 18 may be operated with the same eight pushbuttons (64, 66, 68, 70, 112, 114, 116, 117) as in the full-sized flat panel display embodiment. Of course, other arrangements of switches and controls may be used to operate the near vision test apparatus. In addition to displaying rows of test objects 40 of the same size, rows or columns of test objects 40 of different sizes may be displayed. The test objects 40 may be oriented horizontally or vertically.

Figure 20:
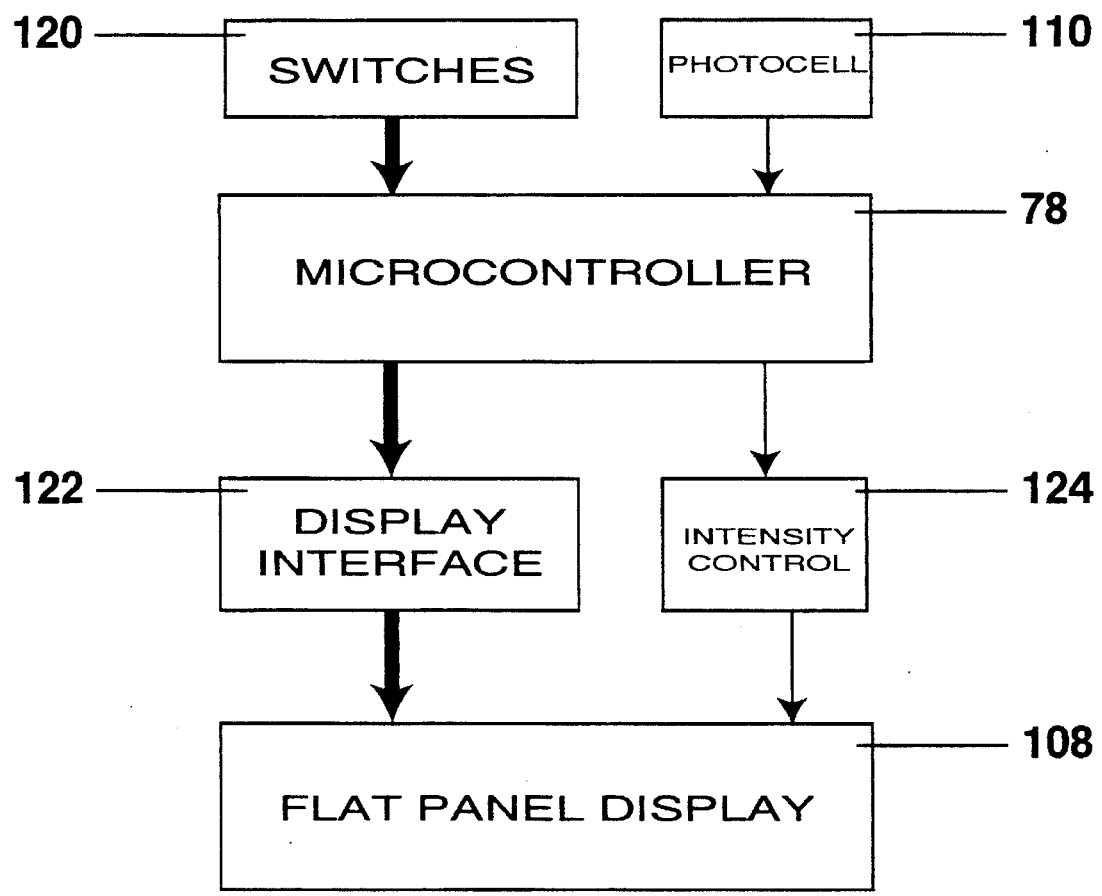
FIG. 20 is a block diagram of a flat panel display embodiment of the invention.

FIG. 20 is a block diagram of a flat panel display embodiment of the invention. The examiner operates the switches 120 in order to select the operational mode of the invention and control the selective display of near vision test objects 40 on the flat panel display 108. The switches 120 may include any of the pushbuttons (64, 66, 68, 70, 112, 114, 116, or 117) that have been described previously. The microcontroller 78 reads the status of the switches 120, and based on the status, the microcontroller 78 generates and sends control and data signals to the display interface 122, which in turn controls the flat panel display 108 so as to display the near vision test objects 40 or other information that has been selected by the examiner. The near vision test objects 40 and other information, such as standardized "HRR" color test plates, special vision tests, or tables of abbreviations, are stored in read-only or other nonvolatile memory which is either a part of the microcontroller 78 or is otherwise accessible to it. The microcontroller 78 may use the same or similar operator interface software that is used in the preferred embodiment, but the control software would be reconfigured to operate the flat panel display 108 through the display interface 122, rather than operate the electroluminescent panels 24.

In FIG. 20, the illumination intensity of the flat panel display 108 may be controlled as is described in reference to FIG. 15. The microcontroller 78 measures, using photocell 110, the amount of incident illumination striking the face of the flat panel display 108, and it commands the intensity control 124 to adjust the level of illumination of the flat panel display 108 so as to maintain a constant degree of contrast illumination between the test objects 40 and the incident illumination striking the front of the flat panel display 108. If the flat panel display 108 is a backlighted liquid crystal display, then the intensity control 124 adjusts the illumination of the lamps that provide the backlighting. If the flat panel display 108 is a plasma or thin film transistor display that inherently provides its own illumination, then the intensity control 124 adjusts a bias signal or other electrical signal in order to control the illumination of the display. The same technique may be used to adjust the contrast illumination in the preferred embodiment of the invention.

Figure 21:
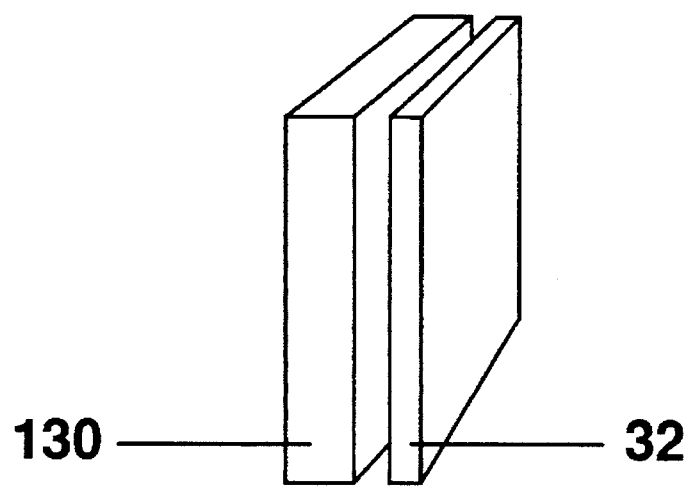
FIG. 21 illustrates an embodiment of the invention that uses a selectively controllable light panel to retroilluminate test objects on a test card.

FIG. 21 illustrates an embodiment of the invention in which a selectively controllable light panel 130 is used to selectively retroilluminate a near vision test card 32. The light panel 130 is positioned parallel and adjacent to the interchangeable test card 32. The light panel 130 may be a thin film transistor display, electroluminescent display, plasma display, or similar display which generates its own light and which is selectively controllable (such as by a microcontroller) to control the emission of light from specific areas on the light panel 130. By controlling the emission of light from specific areas on the light panel 130, the light panel 130 retroilluminates the corresponding specific areas on the test card 32 that are directly in front of the lighted areas on the light panel 130, thereby retroilluminating selected near vision test objects 40 located on the test card 32. The circuitry shown in FIG. 20 may be used to control the selectively controllable light panel 130 by substituting the light panel 130 for the flat panel display 108.

Figure 22:
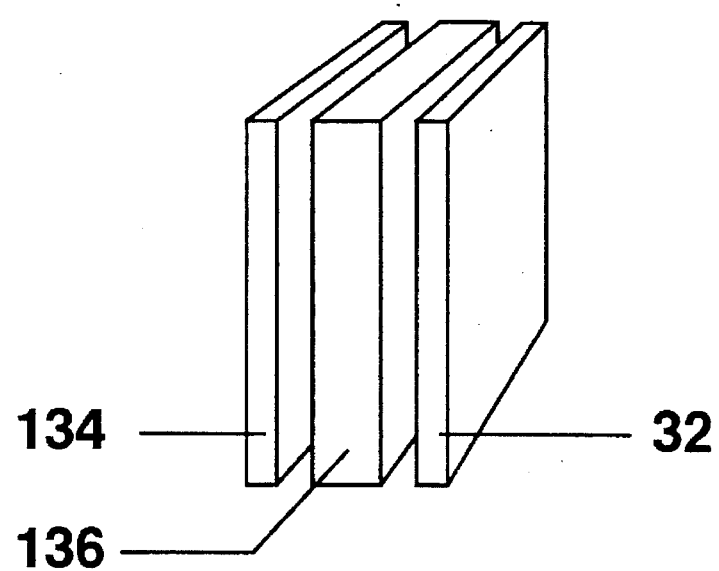
FIG. 22 illustrates an embodiment of the invention that uses a selectively controllable planar light gate to control the transmission of light in order to retroilluminate test objects on a test card.

FIG. 22 illustrates an embodiment of the invention that uses a light source 134 and a selectively controllable planar light gate 136 to control the transmission of light generated by the light source 134 through the light gate 136 in order to selectively retroilluminate a test card 32. The planar light gate 136 is positioned between the light source 134 and the test card 32, and is located adjacent and parallel to the test card 32. The selectively controllable light gate 136 may be a transmissive liquid crystal display, or similar display which is selectively controllable (such as by a microcontroller) to be either opaque or transparent over specific areas on the light gate 136, so as to selectively control the transmission of light from the light source 134 through selected areas of the light gate 136. By controlling the transmission of light through specific areas of the light gate 136, the corresponding specific areas on the test card 32 that are directly in front of the transparent areas of the light gate 136 are retroilluminated by the light source 134, thereby allowing the retroillumination of selected near vision test objects 40 located on the test card 32. The circuitry shown in FIG. 20 may be used to control the selectively controllable light gate 136 by substituting the light gate 136 for the flat panel display 108.

Because certain changes may be made in the above apparatus without departing from the scope of the invention described herein, it is intended that all matter contained in the above description or shown in the accompanying drawings shall be interpreted as illustrative only, and not as limitations to the invention.

A software listing of the program used by the microcontroller 78 to perform the functions described in the preferred embodiment of the invention is provided below in Appendix 1.

Appendix 1

```
TITLE  BRADB.TXT
;(C) COPYRIGHT  WILLIAM BRADFORD PRIESTER AND MAXWELL CUTLER
;   APRIL 1995
; PROGRAM NAME............BRADB.TXT.
; THIS PROGRAM CONSISTS OF 10 PAGES OF ASSEMBLY LANGUAGE FOR THE
; INTEL MICROCONTROLLER  CHIP 8748H
; THIS IS THE SYSTEM FOR THE MATRIX 10 X 3
; WITH  POSITION 1,3 MISSING.
; HARDWARE IS MODEL B OF THE TESTER
; INPUT SWITCHES CONDITIONS:
; (A) SWITCH #1 IS "COMPLETE ROW" DISPLAY, FORWARD OR BACKWARD
; (B) SWITCH #2 IS "INDIVIDUAL" DISPLAY, FORWARD OR BACKWARD
; (C) SWITCH #3 IS "INDIVIDUAL SPECIAL" DISPLAY, FORWARD OR
;   BACKWARD
; (D) SWITCH #4 IS "DIRECTION CHANGER" FORWARD OR BACKWARD
;   ALTERNATELY. ALSO CAUSES EXISTING DISPLAY TO MOVE TO NEXT
; POSITION WHEN IT CHANGES DIRECTION
; (E) SWITCH #3 AND SWITCH #4 OPERATED SIMULTANEOUSLY CAUSE
; "TOTAL DISPLAY" OR "BLANK DISPLAY" ALTERNATELY.
; EACH "ROW" OUTPUT OPERATES A NPN TRANSISTOR, "0" ACTIVATES
; EACH "COLUMN" OUTPUT OPERATES A PNP TRANSISTOR,"1" ACTIVATES.
     ORG 32        ; SCRATCH PAD STARTS FROM POSITION 32
DIRECT:  DS 1      ; DIRECT = 0 GOES FROM ROW 1 TO ROW 10
                   ; DIRECT = 0 GOES FROM COL 1 TO COL 3
                   ; DIRECT = 1 GOES FROM ROW 10 TO ROW 1
                   ; DIRECT = 1 GOES FROM COL 3 TO COL 1
RROW:    DS 1      ; HOLDS THE PATTERN OF THE ROWS 2 -8
                   ; NOTE! '0' IS ACTIVE
CCOL:    DS 1      ; HOLDS THE PATTERN  OF THE 3 COLUMNS AND
                   ; ROWS 1 AND 2
                   ; NOTE! '1' IS ACTIVE
BLROW:   DS 1      ; BLROW = 0, THERE ARE NO 'ROW' DISPLAYS
BLCOL:   DS 1      ; BLCOL = 0, THERE ARE NO 'COLUMN' DISPLAYS
BLALL:   DS 1      ; BLALL = 0, THERE IS NO 'ALL' DISPLAYS
BLSPC:   DS 1      ; BLSPC = 0, THERE IS NO 'SPECIAL' DISPLAYS
TOTAL:   DS 1      ; = 1, ALL THE LIGHTS ON 1 -> 0 SWITCH OFF.
FIRED:   DS 1      ; = 1, LIGHT WAS FIRED: = 0 NOT BEEN FIRED
BINGO:   DS 1      ; = 1 INPUT FROM TWIN SWITCHES.
;
     ORG 0        ; ROM MEMORY
RESET:  JMP  START       ; RESET INSTRUCTION (2 BYTES)
     DB   00
     DW   0000    ; EXTERNAL INTERRUPT VECTOR (ADDR. 3-6)
     DW   0000
     DW   0000    ; TIMER INTERRUPT VECTOR (ADDR. 7-0AH)
     DW   0000
;
;INITIAL HOUSEKEEPING
;SET UP QUASI PORTS P2 AS OUTPUT LINES, NOTE  0= OUTPUTS!
;SET UP QUASI PORTS P1 AS INPUT LINES, NOTE  1 = INPUTS!
START:  MOV A,#000H
     OUTL P2,A    ; P2 ARE OUTPUT LINES
     MOV A,#0FFH
     OUTL P1,A    ; P1 ARE INPUT LINES
;
; INITIALISE ALL OUTPUT LINES TO DEACTIVATE
; NOTE BUS LINES NEED '0' TO ACTIVATE
; P2 LINES NEED '1' TO ACTIVATE (NO INVERTORS USED!)
MOV R0, #RROW
MOV @R0, #000H
MOV R0, #CCOL
MOV @R0, #0FFH
;MOV R0, #TOGGL    ; TOGGLE = 0 FOR "ALL" FUNCTION
;MOV @R0, #000H
MOV R0, #TOTAL
MOV @R0, #000H
; SET UP THE DIRECTION FLAG GOING FORWARD -> AND DOWN
MOV R1, #DIRECT   ; DIRECT =0
MOV @R1,#000H
; SET UP THE FOUR "BLANK" FLAGS
MOV R0,#BLROW    ; BLROW = 0
MOV @R0,#000H
```

```
      MOV R1,#BLCOL   ; BLCOL = 0
      MOV @R1,#000H
      MOV R1,#BLALL   ; BLALL = 0
      MOV @R1,#000H
      MOV R1,#BLSPC   ; BLSPC = 0
      MOV @R1,#000H
      MOV R1,#FIRED   ; FIRED = 0
      MOV @R1,#000H
      MOV R0,#BINGO   ; BINGO = 0
      MOV @R0,#000H
;
; INITIALISE ALL THE POINTERS
      CALL INITPT
      jmp BEGG1
      NOP
ROWWX: JMP ROWW
;
; THIS IS THE INPUT FROM PORT 1 LINE
BEGG1:  IN A,P1
      ANL A, #001H   ;00000001 ....... ROW
      JZ ROWWX
      IN A,P1
      ANL A, #002H   ;00000010 ....... COLUMN
      JZ COLUMN
      IN A,P1
      ANL A, #004H   ;00000100 ....... SPECIAL
      JZ SPECIX
      IN A,P1
      ANL A, #008H   ;00001000 ....... DIRECTION
      JZ DIRECX
      IN A,P1
      JMP BEGG1
DIRECX: JMP DIREC
SPECIX: JMP SPECIL
ALLX:  JMP ALL
; END OF INPUT LOOP
COLUMN: CALL FIFMSC ; ALLOW FOR BALL BOUNCE!
      CALL FIFMSC ; ALLOW FOR BALL BOUNCE!
      CALL FIFMSC ; ALLOW FOR BALL BOUNCE!
COLAMN: IN A,P1
      ANL A, #002H
      JZ COLAMN
  ;   CALL FIFMSC ; ALLOW FOR BALL BOUNCE!
  ;   CALL FIFMSC ; ALLOW FOR BALL BOUNCE!
      CALL FIFMSC ; ALLOW FOR BALL BOUNCE!
      CALL FIFMSC ; ALLOW FOR BALL BOUNCE!
; SWITCH OFF ALL THE FLAGS OF OTHER TYPES
      MOV R1,#BLROW   ; BLANK FLAG OF THE 'ROW'
      MOV @R1,#0
      MOV R1,#BLALL   ; BLANK FLAG OF THE 'ALL'
      MOV @R1,#0
      MOV R1,#BLSPC   ; BLANK FLAG OF THE 'SPECIAL'
      MOV @R1,#0
      MOV R0, #TOTAL
      MOV A, @R0
      JZ COONT
      MOV R0,#TOTAL
      MOV @R0,#0
      CALL INITPT
; THIS IS THE COLUMN PROCEDURE
;;;;;;;;;;;;;;;;;;;;;;;;;
COONT:  MOV R1, #BLCOL
      MOV A,@R1
      JNZ COLL1
; THIS IS A FIRST TIME COLUMN LIGHT WAS OFF!
      MOV R1,#BLCOL   ; SET BLANK FLAG OF THE COLUMN
      MOV @R1,#1
HERE:   MOV A,R7   ; GET THE VALUES OF ROW AND COLL
      MOVP3 A,@A ; DO NOT MOVE POINTER R7!
      MOV R0,#RROW
      MOV @R0,A  ; GET ROW!
      MOV A,R7
```

```
        ADD A, #1
        MOVP3 A,@A
        MOV R0,#CCOL
        MOV @R0,A   ; GET COLUMN
        CALL FIRE   ; LIGHT UP THE DISPLAY
        JMP BEGG1
;
; THE LIGHT WAS LIT AND EVERY INPUT PUSHES ONE PLACE
; FORWARD OR BACK DEPENDING ON DIRECTION
COLL1:  MOV R1, #DIRECT
        MOV A,@R1
        JNZ REVERS
; THIS IS GOING IN A FORWARD DIRECTION
; VERIFY FOR ROW 1 COLUMN 2 AND IF YES PUSH IT FORWARD
; ONE PLACE TO ROW 1 COLUMN 3!!
        MOV A,R3   ;CHECK FOR ROW #1, R3 = 0
        JNZ CWNT   ; NO IT ISN'T
; THIS IS ROW 1
; NOW VERIFY IF WE ARE IN COLUMN 1  R5 =0
        MOV A,R5
        JZ CWNT   ; YES WE ARE IN COLUMN 1 SO JUST CONTINUE
; WE MUST BE IN ROW 1 COLUMN 2 PUSH IT FORWARD ONE PLACE
        INC R7
        INC R7
        INC R6
        INC R6
        INC R5 ; MOVE IT TO COLUMN3
        DEC R4
CWNT:   MOV A,R4  ;SEE IF YOU ARE SITTING AT COLUMN3
        JNZ MIDCOL
; YOU ARE SITTING AT COLUMN 3
        MOV A, R2
        JNZ NEXTRO
;GO BACK TO THE BEGINNING
        CALL INITPT
        JMP HERE
; MOVE TO THE NEXT ROW
NEXTRO: INC R7
        INC R7
        INC R6
        INC R6
        MOV R5,#0
        MOV R4,#2
        DEC R2
        INC R3
        JMP HERE
MIDCOL: INC R7
        INC R7
        INC R6
        INC R6
        INC R5
        DEC R4
        JMP HERE
MADCXL: JMP MADCOL
BACKRX: JMP BACKRO
; THIS IS GOING IN A REVERSE DIRECTION
; IF WE ARE IN ROW 2 AND COLUMN 1 PUSH IT BACK ONE PLACE!
REVERS: MOV A,R5   ;SEE IF YOU ARE SITTING AT COLUMN 1
        JNZ MADCXL  ; NO, THEN GO BACK TO MID OF COLUMN
; YOU ARE SITTING AT COLUMN 1
; NOW CHECK FOR ROW 1
        MOV A,R3   ; CHECKING FOR ROW 1   R3 = 0
        JZ  CBOT
        DEC A    ; CHECK FOR ROW 2     R3 = 1
        JNZ BACKRX ; NOT ROW 2 SO JUST CONTINUE
; THIS IS ROW 2
; MOVE TO THE PREVIOUS ROW
        DEC R7
        DEC R7
        DEC R6
        DEC R6
        MOV R5, #2
```

```
        MOV R4, #0
        DEC R3
        INC R2
        JMP MADCOL ; WE HAVE MOVED TO COLUMN 3
; YOU ARE SITTING AT THE TOP ROW IN THE left HAND CORNER!
;GO BACK TO THE BOTTOM
CBOT:   MOV A,#B1 ; INITIALISE R7 POINTER TO ROW 10, COLUMN 3
        INC A
        INC A
        INC A
        INC A
        MOV R7,A
        MOV A,#B2 ; INITIALISE R6 POINTER TO ROW 10, COLUMN 3
        INC A
        INC A
        INC A
        INC A
        MOV R6,A
        MOV R4,#0
        MOV R5,#2
        MOV R2,#0
        MOV R3,#9
        JMP HERE
; MOVE TO THE PREVIOUS ROW
BACKRO: DEC R7
        DEC R7
        DEC R6
        DEC R6
        MOV R5, #2
        MOV R4, #0
        DEC R3
        INC R2
        JMP HERE
MADCOL: DEC R7
        DEC R7
        DEC R6
        DEC R6
        DEC R5
        INC R4
        JMP HERE
;
ROWW:   CALL FIFMSC ; ALLOW FOR BALL BOUNCE!
        CALL FIFMSC ; ALLOW FOR BALL BOUNCE!
    ;   CALL FIFMSC ; ALLOW FOR BALL BOUNCE!
RAWW:   IN A,P1
        ANL A, #001H
        JZ RAWW
        CALL FIFMSC ; ALLOW FOR BALL BOUNCE!
        CALL FIFMSC ; ALLOW FOR BALL BOUNCE!
    ;   CALL FIFMSC ; ALLOW FOR BALL BOUNCE!
        CALL FIFMSC ; ALLOW FOR BALL BOUNCE!
; SWITCH OFF ALL THE FLAGS OF OTHER TYPES
        MOV R1,#BLCOL   ; BLANK FLAG OF THE 'COL'
        MOV @R1,#0
        MOV R1,#BLALL   ; BLANK FLAG OF THE 'ALL'
        MOV @R1,#0
        MOV R1,#BLSPC   ; BLANK FLAG OF THE 'SPECIAL'
        MOV @R1,#0
        MOV R0, #TOTAL
        MOV A, @R0
        JZ COANT
        MOV R0,#TOTAL
        MOV @R0,#0
        CALL INITPT
; THIS IS THE ROW PROCEDURE
COANT:  MOV R1, #BLROW
        MOV A,@R1
        JNZ ROLL1
; THIS IS A FIRST TIME ROW LIGHTS WERE OFF!
        MOV R1,#BLROW   ; SET BLANK FLAG OF THE COLUMN
        MOV @R1,#1
HEREE:  MOV A,R6    ; GET THE VALUES OF ROW AND COLL
```

```
        MOVP3 A,@A  ; DO NOT MOVE POINTER R7!
        MOV R0,#RROW
        MOV @R0,A   ; GET ROW!
        MOV A,R6
        ADD A, #1
        MOVP3 A,@A
        MOV R0,#CCOL
        MOV @R0,A   ; GET COLUMN
        CALL FIRE   ; LIGHT UP THE DISPLAY
        JMP BEGG1
;
; THE ROW WAS LIT AND EVERY INPUT PUSHES ONE PLACE
; FORWARD OR BACK DEPENDING ON DIRECTION
ROLL1: MOV R1, #DIRECT
        MOV A, @R1
        JNZ REVERZ
; THIS IS GOING IN A FORWARD DIRECTION
    MOV R4,#0   ; SET IT TO COLUMN 3 FOR FORWARD
    MOV A,R4  ;SEE IF YOU ARE SITTING AT COLUMN3
    JNZ MIDROW
; YOU ARE SITTING AT COLUMN 3
    MOV A, R2
    JNZ NEXTRA
;GO BACK TO THE BEGINNING
        CALL INITPT
        JMP HEREE
; MOVE TO THE NEXT ROW
NEXTRA: INC R6
        INC R6
        INC R6
        INC R6
        INC R6
        INC R7
        INC R7
        INC R7
        INC R7
        INC R7
        MOV R5,#0
        MOV R4,#2
        DEC R2
        INC R3
        JMP HEREE
MIDROW: INC R6
        INC R6
        INC R7
        INC R7
        INC R5
        DEC R4
        JMP HEREE
; THIS IS GOING IN A REVERSE DIRECTION
REVERZ:  MOV R5,#0 ; PLACE AT COLUMN 1
        MOV A,R5  ;SEE IF YOU ARE SITTING AT COLUMN 1
    JNZ MADROW
; YOU ARE SITTING AT COLUMN 1
    MOV A,R3
    JNZ BACKRA
; YOU ARE SITTING AT THE TOP ROW IN THE left HAND CORNER!
;GO BACK TO THE BOTTOM
        MOV A,#B2 ; INITIALISE R6 POINTER TO ROW 10, COLUMN 3
        MOV R6,A
        MOV A,#B1 ; INITIALISE R6 POINTER TO ROW 10, COLUMN 3
        MOV R7,A
        MOV R4,#0
        MOV R5,#2
        MOV R2,#0
        MOV R3,#9
        JMP HEREE
; MOVE TO THE PREVIOUS ROW
BACKRA: DEC R6
        DEC R6
```

```
        DEC R6
        DEC R6
        DEC R6
        DEC R6
        DEC R7
        DEC R7
        DEC R7
        DEC R7
        DEC R7
        MOV R5,#1   ;GO TO COLUMN 1 OTHERWISE NO DISPLAY
        MOV R4,#1
        DEC R3
        INC R2
        JMP HEREE
MADROW: DEC R6
        DEC R6
        DEC R7
        DEC R7
        DEC R5
        INC R4
        JMP HEREE
;
; END OF ROW PROCEDURE
DIREC:  CALL FIFMSC ; ALLOW FOR BALL BOUNCE!
        CALL FIFMSC ; ALLOW FOR BALL BOUNCE!
        CALL FIFMSC ; ALLOW FOR BALL BOUNCE!
DARACT: IN A,P1
        ANL A,#004H ; LOOK FOR A SECOND INPUT!
        JNZ DARACC
        MOV R1,#BINGO
        MOV @R1,#1
        JMP DARACT
DARACC: IN A,P1
        ANL A,#008H
        JZ DARACT
        CALL FIFMSC ; ALLOW FOR BALL BOUNCE!
        CALL FIFMSC ; ALLOW FOR BALL BOUNCE!
        MOV R1,#BINGO
        MOV A,@R1   ; CHECK FOR DOUBLE INPUT!
        JZ DAAR     ; NO THERE IS NOT
; YES THERE IS A DOUBLE INPUT
        MOV R1,#BINGO
        MOV @R1,#0  ; RESET FLAG
        JMP ALL
DAAR:   MOV R0, #TOTAL
        MOV @R0, #000H
; THIS IS THE DIRECTION PROCEDURE
MOV R1, #DIRECT   ; TOGGLES THE DIRECTIONS!
MOV A, @R1
XRL A, #1
MOV @R1, A
;
MOV R0,#BLCOL
MOV A,@R0
JNZ CCCOLL   ; FOUND COLUMN DISPLAY
MOV R0,#BLROW
MOV A,@R0
JNZ RRROWW;  ; FOUND ROW DISPLAY
MOV R0,#BLSPC
MOV A,@R0
JNZ SPECCC   ; FOUND SOECIAL DISPLAY
JMP BEGG1
CCCOLL: JMP COONT
RRROWW: JMP COANT
SPECCC: JMP SPEC1
CAANTX: JMP CAANT
SPECIL: CALL FIFMSC ; ALLOW FOR BALL BOUNCE!
        CALL FIFMSC ; ALLOW FOR BALL BOUNCE!
      ; CALL FIFMSC ; ALLOW FOR BALL BOUNCE!
SPACIL: IN A,P1
        ANL A,#008H ; LOOK FOR A SECOND INPUT!
```

```
            JNZ SPACC
            MOV R1,#BINGO
            MOV @R1,#1
            JMP SPACIL
SPACC:   IN A,P1
            ANL A,#004H
            JZ SPXCIL
            CALL FIFMSC ; ALLOW FOR BALL BOUNCE!
            CALL FIFMSC ; ALLOW FOR BALL BOUNCE!
            MOV R1,#BINGO
            MOV A,@R1  ; CHECK FOR DOUBLE INPUT!
            JZ SPUC    ; NO THERE IS NOT
; YES THERE IS A DOUBLE INPUT
            MOV R1,#BINGO
            MOV @R1,#0  ; RESET FLAG
            JMP ALL
SPXCIL: JMP SPACIL
SPUC:   CALL FIFMSC ; ALLOW FOR BALL BOUNCE!
            CALL FIFMSC ; ALLOW FOR BALL BOUNCE!
; THIS IS THE SPECIAL NUMBER PROCEDURE
; SWITCH OFF ALL THE FLAGS OF OTHER TYPES
        MOV R1,#BLCOL   ; BLANK FLAG OF THE COLUMN
        MOV @R1,#0
        MOV R1,#BLALL   ; BLANK FLAG OF THE ALL
        MOV @R1,#0
        MOV R1,#BLROW   ; BLANK FLAG OF THE ROW
        MOV @R1,#0
        MOV R0, #TOTAL
        MOV A, @R0
        JZ CAANT
        MOV R0,#TOTAL
        MOV @R0,#0
        CALL INITPT
        NOP
        NOP
CAANT: MOV R1,#BLSPC
        MOV A,@R1
        JNZ SPEC1X
        JMP COANTT
SPEC1X: JMP SPEC1

CNTTX: JMP CNTT
CNTT0X: JMP CNTT0
; THIS IS A FIRST TIME, SPECIAL LIGHT WAS OFF!
COANTT: MOV R1,#BLSPC   ; SET BLANK FLAG OF THE 'SPECIAL'
        MOV @R1,#1
SPEC1: MOV A,R7   ; CHECK IF LINE SHOULD OPERATE
        ADD A,#61  ; VALUE FROM OTHER TABLE LOOKING FOR 000H IN
                ; COLUMN !!!
        MOVP3, A,@A
        JNZ CNTT0
; WE HAVE FOUND A SPECIAL LINE!!!
; SEE IF IT HAS BEEN FIRED
        MOV R1, #FIRED
        MOV A,@R1
        JNZ CNTT0     ; YES IT HAS BEEN FIRED
; NO IT WAS NOT FIRED
        MOV R1, #FIRED
        MOV @R1,#1    ; SET IT TO FIRED = 1
        JMP HERE ; CAN LIGHT THROUGH THE COLUMN ROUTINE
RXVORS: JMP ROVORS
CXNTT: JMP CONTT
TXPPP: JMP TOPPP
CNTT0: MOV R1,#FIRED
        MOV @R1,#0    ; RESET FLAG TO FIRED = 0
CNTT:  MOV R1,#DIRECT   ; FIND OUT WHICH DIRECTION TO GO
        MOV A,@R1
        JNZ ROVORS    ; GO IN REVERSE, DIRECT = 1
; THIS IS THE FORWARD DIRECTION
; 1. CHECK FOR END OF LINE
        MOV A,R4
        JNZ CONTT; NOT END OF LINE
```

```
; THIS IS THE END OF A LINE
    MOV R5,#0
    MOV R4,#2
    NOP
    MOV A,R2 ; NOW CHECK FOR LAST LINE
    JZ TOPPP ; IT WAS THE LAST LINE
    INC R3    ; MOVE TO THE NEXT LINE
    DEC R2
    JMP CONTT1
; START AT TOP
    ; INITIALISE ALL THE POINTERS
TOPPP: MOV A,#T1 ; INITIALISE R7 POINTER TO ROW 1, COLUMN 1
    MOV R7,A
    MOV A,#T2 ; INITIALISE R6 POINTER TO ROW 1, COLUMN 1
    MOV R6,A   ; SECOND BLOCK
    MOV R5,#0
    MOV R4,#2
    MOV R3,#0
    MOV R2,#9
    JMP SPEC1
CONTT:  INC R5
    DEC R4
CONTT1: INC R7
    INC R7
    INC R6
    INC R6
    JMP SPEC1
CENTTX: JMP CENTT
BOTTTX: JMP BOTT
;THIS IS THE REVERSE DIRECTION
; 1. CHECK FOR END OF LINE
ROVORS: MOV A,R5
    JNZ CENTTX; NOT END OF LINE
; THIS IS THE END OF A LINE
    MOV R5,#2
    MOV R4,#0
    MOV A,R3 ; NOW CHECK FOR THE TOP LINE
    JZ BOTT ; IT WAS THE TOP LINE
    INC R2    ; MOVE TO THE NEXT LINE
    DEC R3
    JMP CENTT1
; START AT BOTTOM
    ; INITIALISE ALL THE POINTERS
BOTT:   MOV A,#B1 ; INITIALISE R7 POINTER TO ROW 10, COLUMN 3
    MOV R7,A
    MOV A,#B2 ; INITIALISE R6 POINTER TO ROW 10, COLUMN 3
    MOV R6,A  ; SECOND BLOCK
    INC R7   ; MOVE IT ALONG 4 PLACES
    INC R7
    INC R7
    INC R7
    INC R6   ; MOVE IT ALONG 4 PLACES
    INC R6
    INC R6
    INC R6
    MOV R5,#2
    MOV R4,#0
    MOV R3,#9
    MOV R2,#0
    JMP SPEC1
CENTT:  DEC R5
    INC R4
CENTT1: DEC R7
    DEC R7
    DEC R6
    DEC R6
    JMP SPEC1
;
; THIS IS THE "ALL" OR "BLANK" PROCEDURE
; SWITCH OFF ALL THE FLAGS OF OTHER TYPES
ALL:    MOV R1,#BLROW    ; BLANK FLAG OF THE ROW
    MOV @R1,#0
```

```
        MOV R1,#BLCOL   ; BLANK FLAG OF THE COLUMN
        MOV @R1,#0
        MOV R1,#BLSPC   ; BLANK FLAG OF THE 'SPECIAL'
        MOV @R1,#0
;
; IF LIGHTS "ON" TURN THEM "OFF"
; OR IF LIGHTS "OFF" TURN THEM "ON"
; TOTAL = 1 INDICATES LIGHTS ARE "ON"
        MOV R0,#TOTAL
        MOV A,@R0
        JNZ OFFF ; TURN OFF THESE LIGHTS!
        ; TURN ON THESE LIGHTS!
        CALL INITPT ; INITIALISE POINTERS
        MOV R0,#TOTAL ; TOTAL = 1
        MOV @R0,#1
; SWITCH ON COLUMN
        MOV A,#018H  ; 00011000
        MOV R0,#CCOL
        MOV @R0,A
; SWITCH ON ROW
        MOV A,#0FFH  ; 11111111
        MOV R0,#RROW
        MOV @R0,A
        JMP BING
OFFF:   MOV R0,#TOTAL ; TOTAL = 0
        MOV @R0,#0
; SWITCH OFF COLUMN
        MOV A,#008H  ; 00000111
        MOV R0,#CCOL
        MOV @R0,A
; SWITCH OFF ROW
        MOV A,#000H  ; 000000000
        MOV R0,#RROW
        MOV @R0,A
BING:   CALL FIRE  ; INPUT TO THE LIGHTS
        JMP BEGG1
;
; HERE STARTS THE SUBROUTINES
;
FIRE: MOV R0,#RROW  ; SET UP THE ROWS
      MOV A,@R0
      OUTL BUS,A
      MOV R0,#CCOL  ; SET UP THE COLUMNS
      MOV A,@R0
      OUTL P2,A
      RET
;
; SETT THE POINTER TO THE FIRST POSITION
;POINTERS:
; (1) R7 STAYS IN COLUMN 1 OF EVERY ROW
; (2) R6 GOES TO EACH MEMORY LOCATION IN QUESTION
; (3) R5 =0 DETERMINES COLUMN 1, R4 =0 DETERMINES COLUMN 3
; (4) R3 =0 DETERMINES ROW 1, R2 =0 DETERMINES ROW 10
;
; INITIALISE ALL THE POINTERS
INITPT: MOV A,#T1 ; INITIALISE R7 POINTER TO ROW 1, COLUMN 1
        MOV R7,A  ; block 1
        MOV A,#T2 ; INITIALISE R6 POINTER TO ROW 1, COLUMN 1
        MOV R6,A  ; block 2
        MOV R5,#0
        MOV R4,#2
        MOV R3,#0
        MOV R2,#9
        RET
;
;
; FIFTY MSEC DELAY
; CYCLE TIME IS = 15 *XTAL OSC PERIOD
;FOR 4MHZ XTAL, CYCLE TIME = 15*.25USEC=3.75USEC
;50 MSEC=20*(133*(3.75*5)+3.75*5)
;FIFMSC: SEL RB1
FIFMSC: MOV R0,#20
```

```
D0:     MOV R1,#133
D1:     NOP        ;1 CYCLE
        DEC R1     ;1 CYCLE
        MOV A,R1   ;1 CYCLE
        JNZ D1     ;2 CYCLES TOTAL 5 CYCLES
        NOP        ;1 CYCLE
        DEC R0     ;1 CYCLE
        MOV A,R0   ;1 CYCLE
        JNZ D0     ;2 CYCLES TOTAL 5 CYCLES
;       SEL RB0
        RET
;
; MAKE SURE THE LOOK UP TABLES APPEAR IN PAGE 3
;       DW 0000,0000,0000,0000,0000,0000,0000,0000,0000,0000
        DW 0000,0000,0000,0000,0000,0000,0000,0000,0000,0000
        DW 0000,0000,0000,0000,0000,0000,0000,0000,0000,0000
; ENTER HERE THE ROM LOOK UP TABLES
; NOTE "DB" IS FIRST THEN "P2" IS SECOND
;DB IS ALL ROWS P2 IS PART ROWSAND COLUMNS
TOPP:   DB 000H,00BH,000H,00DH,000H,007H
        DB 000H,013H,000H,015H,000H,016H
        DB 001H,003H,001H,005H,001H,006H
        DB 002H,003H,002H,005H,002H,006H
        DB 004H,003H,004H,005H,004H,006H
        DB 008H,003H,008H,005H,008H,006H
        DB 010H,003H,010H,005H,010H,006H
        DB 020H,003H,020H,005H,020H,006H
        DB 040H,003H,040H,005H,040H,006H
BOTT:   DB 080H,003H,080H,005H,080H,006H
;   LOOK UP TABLE FOR THE RANDOM LIST
; SEARCH FOR 000H IN "COLUMN" SECOND POSITION, 61 OFFSETT!!!
;
        DB 000H,00BH,000H,000H,000H,007H
        DB 000H,013H,000H,015H,000H,000H
        DB 001H,000H,001H,005H,001H,006H
        DB 002H,003H,002H,000H,002H,006H
        DB 004H,000H,004H,005H,004H,006H
        DB 008H,003H,008H,005H,008H,000H
        DB 010H,003H,010H,000H,010H,006H
        DB 020H,003H,020H,005H,020H,000H
        DB 040H,003H,040H,000H,040H,006H
        DB 080H,000H,080H,005H,080H,006H
;
TOPP2:  DB 000H,008H,000H,008H,000H,007H
        DB 000H,010H,000H,010H,000H,010H
        DB 001H,000H,001H,000H,001H,000H
        DB 002H,000H,002H,000H,002H,000H
        DB 004H,000H,004H,000H,004H,000H
        DB 008H,000H,008H,000H,008H,000H
        DB 010H,000H,010H,000H,010H,000H
        DB 020H,000H,020H,000H,020H,000H
        DB 040H,000H,040H,000H,040H,000H
BOTT2:  DB 080H,000H,080H,000H,080H,000H
;
T1      EQU TOPP-0300H
B1      EQU BOTT-0300H
T2      EQU TOPP2-0300H
B2      EQU BOTT2-0300H
END
```

We claim:

1. A near vision test apparatus for use by a healthcare examiner, comprising:
   (a) a generally rectilinear device having a front face and a generally parallel rear face, said device sized to be held by a healthcare examiner in a single hand while being operated by said single holding hand, wherein said from face is a near vision test card having a plurality of near vision test objects affixed thereon, said test objects arranged in one or more rows and one or more columns on said test card;
   (b) a plurality of electroluminescent panels positioned between said front face and said rear face, said electroluminescent panels oriented to retroilluminate said test objects;
   (c) a plurality of switches accessible on the outside of said device, wherein said switches are operable by said holding hand of said examiner to both select one of a plurality of operational modes of said device and to select the retroillumination of certain of said test objects; and
   (d) a microcontroller responsive to said switches, wherein said microcontroller selectively activates said electroluminescent panels to selectively retroilluminate said test objects in response to the operation of said switches by said holding hand of said examiner.

2. A near vision test apparatus for use by a healthcare examiner, comprising:
   (a) a generally rectilinear device having a front face and a generally parallel rear face, said device sized to be held by a healthcare examiner in a single hand while being operated by said single holding hand, wherein said front face is a near vision test card having a plurality of near vision test objects affixed thereon, said test objects arranged in one or more rows and one or more columns on said test card;
   (b) at least one selectively controllable planar light panel positioned parallel to and to the rear of said front face, said light panel oriented to retroilluminate said test objects;
   (c) a plurality of switches accessible on the outside of said device, wherein said switches are operable by said holding hand of said examiner to both select one of a plurality of operational modes of said device and to select the retroillumination of certain of said test objects; and
   (d) a microcontroller responsive to said switches, wherein said microcontroller selectively controls the emission of light from certain areas on said light panel to selectively retroilluminate said test objects in response to the operation of said switches by said holding hand of said examiner.

3. A near vision test apparatus for use by a healthcare examiner, comprising:
   (a) a generally rectilinear device having a front face and a generally parallel rear face, said device sized to be held by a healthcare examiner in a single hand while being operated by said single holding hand, wherein said front face is a near vision test card having a plurality of near vision test objects affixed thereon, said test objects arranged in one or more rows and one or more columns on said test card;
   (b) at least one selectively controllable planar light gate positioned adjacent, parallel, and to the rear of said test card;
   (c) at least one light source positioned between said light gate and said rear face, said light source oriented to retroilluminate said test objects by light transmission through said light gate;
   (d) a plurality of switches accessible on the outside of said device, wherein said switches are operable by said holding hand of said examiner to both select one of a plurality of operational modes of said device and to select the retroillumination of certain of said test objects; and
   (e) a microcontroller responsive to said switches, wherein said microcomroller selectively controls the transmission of light through certain areas on said light gate to selectively retroilluminate said test objects in response to the operation of said switches by said holding hand of said examiner.

4. A near vision test apparatus for use by a healthcare examiner, comprising:
   (a) a generally rectilinear device having a front face and a generally parallel rear face, said device sized to be held by a healthcare examiner in a single hand while being operated by said single holding hand, wherein said from face is an electronic flat panel display capable of displaying with or without illumination a plurality of near vision test objects, a plurality of advanced vision tests, and a plurality of ophthalmic reference tables;
   (b) a plurality of switches accessible on the outside of said device, wherein said switches are operable by said holding hand of said examiner to both select one of a plurality of operational modes of said device and to select certain said test objects, said advanced vision tests, or said ophthalmic reference tables for display with or without illumination on said flat panel display; and
   (c) a microcontroller responsive to said switches, wherein said microcontroller selectively displays with or without illumination one or more of said near vision test objects, said advanced vision tests, or said ophthalmic reference tables on said flat panel display in response to the operation of said switches by said holding hand of said examiner.

5. A near vision test apparatus for use by a healthcare examiner, comprising:
   (d) a generally rectilinear device having a front face and a generally parallel rear face, said device sized to be held by a healthcare examiner in a single hand while being operated by said single holding hand, wherein said from face is a near vision test card having a plurality of near vision test objects affixed thereon, said test objects arranged in one or more rows and one or more columns on said test card;
   (e) means for selectively retroilluminating one or more of said near vision test objects; and
   (f) means, operable by said holding hand of said examiner, for controlling said selective retroillumination of said near vision test objects.

6. The apparatus of claim 5, wherein said means for selectively retroilluminating operates by selectively activating one or more light sources located inside said device between said test card and said rear face, said light sources oriented to retroilluminate said test objects.

7. The apparatus of claim 5, wherein said means for selectively retroilluminating operates by selectively controlling the transmission of light from one or more light sources located inside said device through certain areas on a planar light gate positioned between said light source and said test card, said light gate aligned parallel to and adjacent to said test card.

8. The apparatus of claim 5, wherein said means for selectively retroilluminating operates by selectively controlling the emission of light from certain areas on a planar light panel positioned parallel, adjacent, and to the rear of said test card, said light panel oriented to retroilluminate said test objects.

9. The apparatus of claim 5, further comprising means for removably securing said test card, whereby said test card may easily be interchanged with a different test card.

10. The apparatus of claim 5, further comprising means for removably securing said device to a protruding reading card rod of a phoropter or to a plurality, of integrated physical examination equipment.

11. The apparatus of claim 5, wherein said rear face includes a means for indicating which of said test objects are selectively retroilluminated.

12. The apparatus of claim 5, wherein said means for controlling consists of a plurality of switches accessible on said device.

13. The apparatus of claim 12, wherein said switches include "change row", "change column", "intensive care ", and "direction ".

14. The apparatus of claim 12, further comprising a means, responsive to said means for controlling, for selecting one of a plurality of operational modes of said device, wherein said operational modes include "change row", "change column", "intensive care", "direction", and "all".

15. The apparatus of claim 14, wherein said "direction" operational mode allows said examiner to change direction of selective retroillumination of said test objects while using other said operational modes.

16. The apparatus of claim 14, wherein said "intensive care" operational mode allows the selective retroillumination of only said test objects representing the numerals "2", "3", "4", and "5", whereby a mechanically-ventilated or otherwise speech-impaired patient may signal test responses in a non-verbal manner.

17. The apparatus of claim 14, wherein said rear face includes a means for indicating which of said operational modes is selected by the examiner.

18. A near vision test apparatus for use by a healthcare examiner, comprising:

(a) a generally rectilinear device having a front face and a generally parallel rear face, said device sized to be held by a healthcare examiner in a single hand while being operated by said single holding hand, wherein said from face is an electronic flat panel display capable of displaying with or without illumination a plurality of near vision test objects, a plurality of advanced vision tests, and a plurality of ophthalmic reference tables;

(b) means for selectively displaying with or without illumination said near vision test objects, said advanced vision tests, or said ophthalmic reference tables on said flat panel display; and (c) means, operable by said holding hand of said examiner, for both controlling said selective display and illumination of said near vision test objects, said advanced vision tests, and said ophthalmic reference tables and selecting one of a plurality of operational modes of said device.

19. The apparatus of claim 18, wherein said rear face includes a means for indicating which of said test objects or said advanced vision tests are selectively displayed and illuminated on said flat panel display.

20. The apparatus of claim 18, further comprising means for removably securing said device to a protruding reading card rod of a phoropter or to a plurality of integrated physical examination equipment.

21. The apparatus of claim 18, wherein said means for controlling consists of a plurality of switches accessible on said device.

22. The apparatus of claim 21, wherein said switches include "change row", "change column", "intensive care", "direction", "randomize test objects", "change style of test objects", "change advanced vision test", and "change reference table".

23. The apparatus of claim 22, wherein said operational modes include "change row", "change column", "intensive care", "direction", "all", "randomize test objects", "change style of test objects", "change advanced vision test", and "change reference table".

24. The apparatus of claim 23, wherein said "direction" operational mode allows said examiner to change direction of said selective illuminated display of said test objects, said advanced vision tests, and said ophthalmic reference tables.

25. The apparatus of claim 23, wherein said "intensive care" operational mode allows said selective illuminated display of only said test objects representing the numerals "2", "3", "4", and "5", whereby a mechanically-ventilated or otherwise speech-impaired patient may signal test responses in a non-verbal manner.

26. The apparatus of claim 23, further comprising means for indicating which of said operational modes is selected by the examiner.

27. A method of conducting a near vision test by a healthcare examiner, comprising the steps (a) positioning a hand-held near vision test apparatus in front of a patient, said examiner holding said apparatus in a single hand;

(b) selecting, using said holding hand of said examiner, one of a plurality of operational modes of said near vision test apparatus, whereby said examiner's second hand is free to perform other necessary tasks, such as covering said patient's eye not being tested;

(c) operating, using said holding hand of said examiner, said near vision test apparatus to selectively retroilluminate or selectively display with or without illumination one or more near vision test objects of various sizes on said near vision test apparatus, so as to direct said patient's attention to said illuminated near vision test objects and so that said near vision test may be administered without regard to the position of said patient's body;

(d) obtaining feedback from said patient, wherein said feedback consists of said patient's attempt to identify said illuminated near vision test objects;

(e) comparing said feedback from said patient with said illuminated near vision test objects;

(f) changing said illuminated test objects in response to said comparison and (g) determining a level of visual acuity of said patient by repeating at least steps (c) through (f), wherein said level of visual acuity corresponds to the smallest size of said test objects that said patient can identify.

* * * * *